US012690963B2

(12) United States Patent
Maimon et al.

(10) Patent No.: US 12,690,963 B2
(45) Date of Patent: Jul. 28, 2026

(54) PROSTHETIC HEART VALVE HAVING COMMISSURE SUPPORT ELEMENT

(71) Applicant: Edwards Lifesciences Corporation, Irvine, CA (US)

(72) Inventors: David Maimon, Atlit (IL); Michael Bukin, Pardes Hanna (IL); Tamir S. Levi, Zikhron Yaakov (IL); Noam Nir, Pardes-Hanna (IL); Ziv Yohanan, Kfar Hahoresh (IL); Amir Keret, Tirat Hacarmel (IL); Elena Sherman, Pardes Hana (IL)

(73) Assignee: Edwards Lifesciences Corporation, Irvine, CA (US)

( * ) Notice: Subject to any disclaimer, the term of this patent is extended or adjusted under 35 U.S.C. 154(b) by 1016 days.

(21) Appl. No.: 17/320,004

(22) Filed: May 13, 2021

(65) Prior Publication Data

US 2021/0259833 A1     Aug. 26, 2021

Related U.S. Application Data

(63) Continuation of application No. PCT/US2019/061392, filed on Nov. 14, 2019.

(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2427* (2013.01)

(58) Field of Classification Search
CPC .... A61F 2/2418; A61F 2/2409; A61F 2/2427; A61F 2220/0033; A61F 2220/0091; A61F 2/2412; A61F 2/24
See application file for complete search history.

(56) References Cited

U.S. PATENT DOCUMENTS 3,409,013 A     11/1968 Berry
3,548,417 A     12/1970 Kisher
(Continued)

FOREIGN PATENT DOCUMENTS

CN     215425315 U     1/2022
DE     0144167 C     9/1903
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Yashita Sharma
*Assistant Examiner* — Kia Xiong White
(74) *Attorney, Agent, or Firm* — Klarquist Sparkman, LLP

(57) ABSTRACT

A prosthetic heart valve includes an annular frame including a plurality of angled strut members that is radially collapsible to a collapsed configuration and radially expandable to an expanded configuration. The frame has an inflow end and an outflow end, and includes a leaflet structure positioned within the frame, the leaflet structure comprising a plurality of leaflets arranged to form a plurality of commissures. The frame includes a plurality of commissure support elements, each commissure support element being positioned at one of the commissures. Each of the commissure support elements has a coupling portion coupled to the frame and first and second members coupled to the coupling portion and extending in a direction toward the inflow end of the frame or toward the outflow end of the frame. The leaflets of each commissure are received between the first and second members of the respective commissure support element.

28 Claims, 27 Drawing Sheets

Related U.S. Application Data

(60) Provisional application No. 62/767,412, filed on Nov. 14, 2018.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,730,118 B2 * | 5/2004 | Spenser ................ A61F 2/9524 |
| | | | 623/1.24 |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |

(56)                    References Cited

U.S. PATENT DOCUMENTS

| | | | |
|---|---|---|---|
| 7,510,575 B2 | 3/2009 | Spenser et al. | |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,291,570 B2 | 10/2012 | Fidenschink et al. | |
| 8,348,998 B2 | 1/2013 | Pintor et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,685,055 B2 | 4/2014 | VanTassel et al. | |
| 8,747,463 B2 | 6/2014 | Fogarty et al. | |
| 9,078,781 B2 | 7/2015 | Ryan et al. | |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0040791 A1 | 2/2003 | Oktay | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1* | 2/2004 | Spenser | A61F 2/243 |
| | | | 623/2.14 |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0137686 A1 | 6/2005 | Salahieh et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1* | 8/2007 | Salahieh | A61F 2/2436 |
| | | | 623/2.11 |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0004735 A1 | 1/2010 | Yang et al. | |
| 2010/0049313 A1 | 2/2010 | Alon et al. | |
| 2010/0082094 A1 | 4/2010 | Quadri et al. | |
| 2010/0100176 A1 | 4/2010 | Elizondo et al. | |
| 2010/0168844 A1 | 7/2010 | Toomes et al. | |
| 2010/0185277 A1 | 7/2010 | Braido et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0030090 A1 | 2/2012 | Johnston et al. | |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2013/0023985 A1 | 1/2013 | Khairkhahan et al. | |
| 2013/0046373 A1 | 2/2013 | Cartledge et al. | |
| 2013/0150956 A1* | 6/2013 | Yohanan | A61F 2/2418 |
| | | | 623/2.14 |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1* | 10/2014 | Cartledge | A61F 2/95 |
| | | | 623/1.11 |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2016/0175095 A1 | 6/2016 | Dienno et al. | |
| 2016/0175096 A1* | 6/2016 | Dienno | A61F 2/2415 |
| | | | 623/2.13 |
| 2016/0374802 A1 | 12/2016 | Levi et al. | |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Evi et al. | |
| 2019/0192289 A1 | 6/2019 | Levi et al. | |

(56) References Cited

U.S. PATENT DOCUMENTS

FOREIGN PATENT DOCUMENTS

| | | | |
|---|---|---|---|
| DE | 2246526 | A1 | 3/1973 |
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | A1 | 3/1984 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| JP | 2017538518 | A | 12/2017 |
| SU | 1271508 | A1 | 11/1986 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9829057 | A1 | 7/1998 |
| WO | 9930646 | A1 | 6/1999 |
| WO | 9933414 | A1 | 7/1999 |
| WO | 9940964 | A1 | 8/1999 |
| WO | 9947075 | A1 | 9/1999 |
| WO | 0018333 | A1 | 4/2000 |
| WO | 0041652 | A1 | 7/2000 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0047139 | A9 | 9/2001 |
| WO | 0164137 | A1 | 9/2001 |
| WO | 0176510 | A2 | 10/2001 |
| WO | 0222054 | | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | | 6/2003 |
| WO | 2005034812 | A1 | 4/2005 |
| WO | 2005055883 | A1 | 6/2005 |
| WO | 2005084595 | A1 | 9/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | WO-2016144708 | A1 | 9/2016 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.
Walther T, Dehdashtian MM, Khanna R, Young E, Goldbrunner PJ, Lee W. Trans-catheter valve-in-valve implantation: In vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.
Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.
Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.
Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

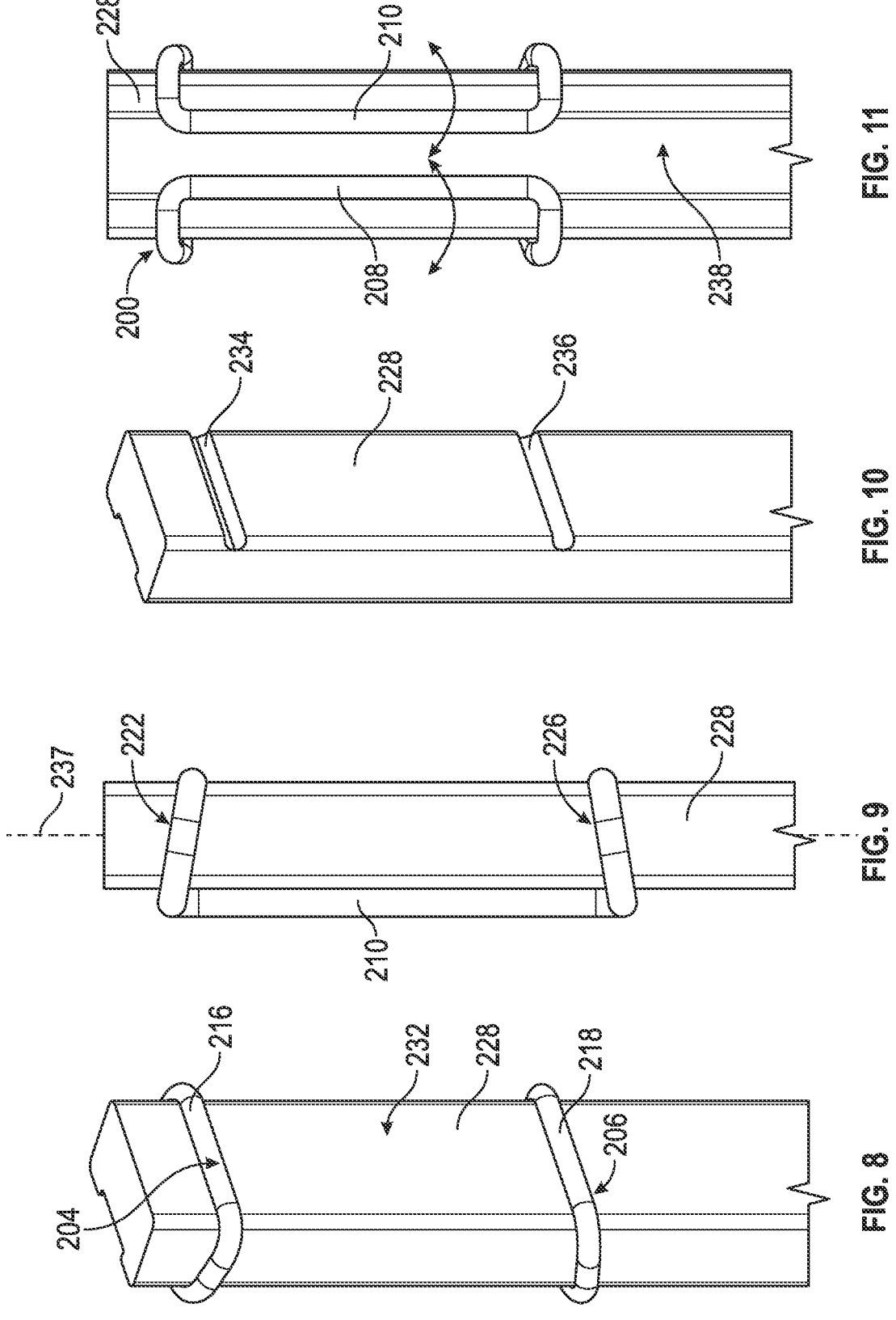

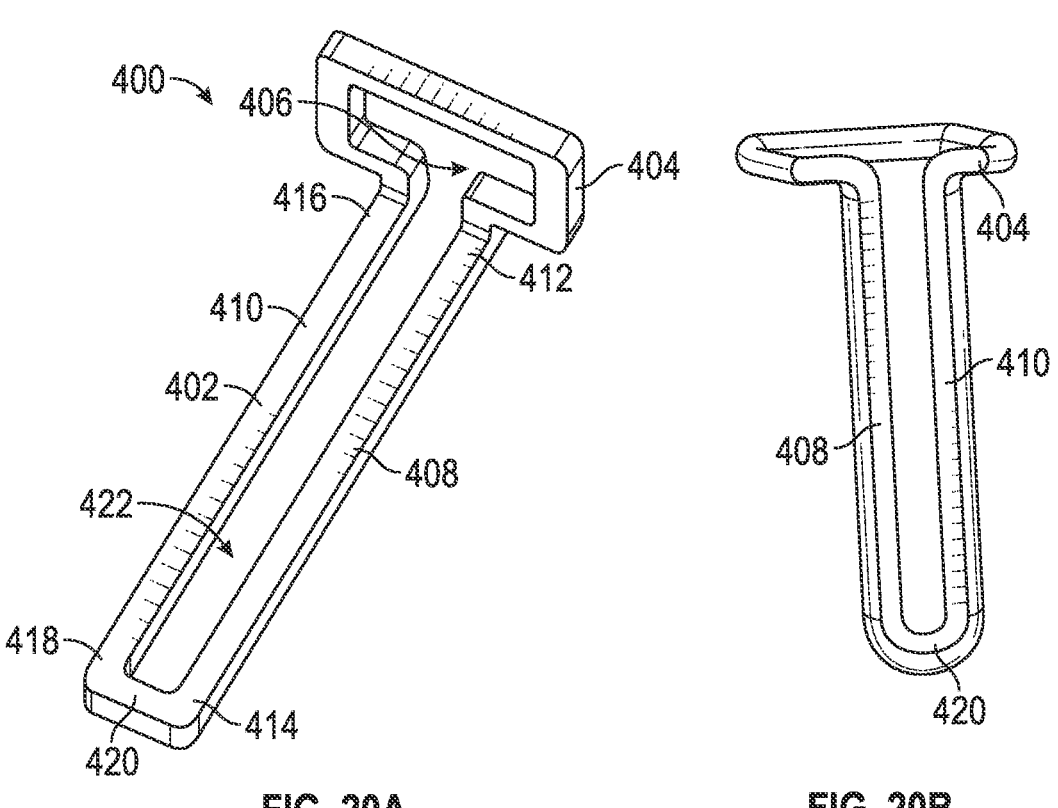
FIG. 20A
FIG. 20B
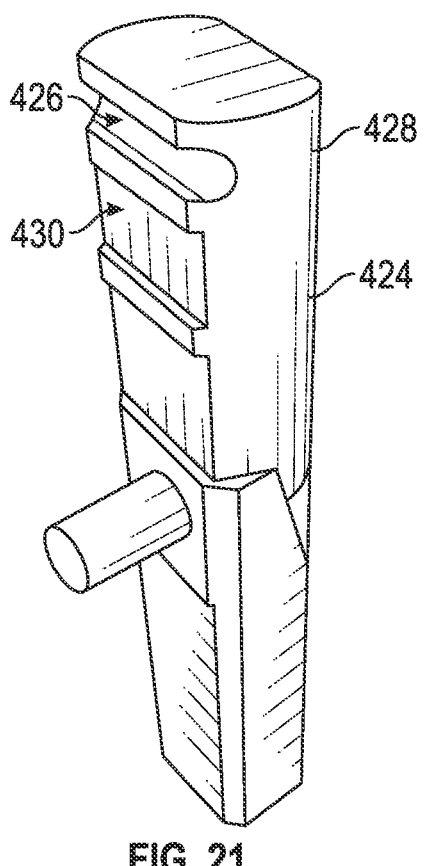
FIG. 21

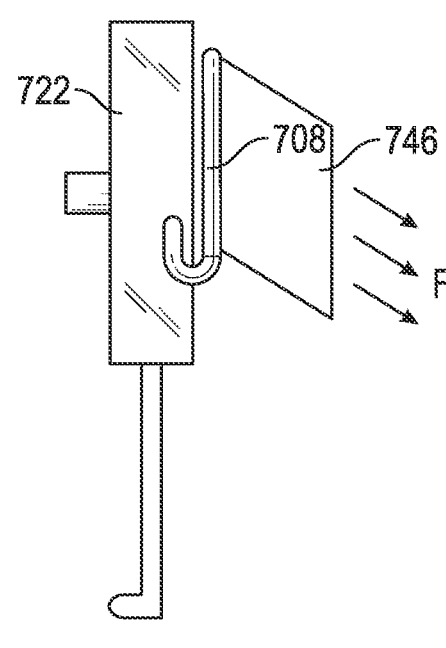
FIG. 40
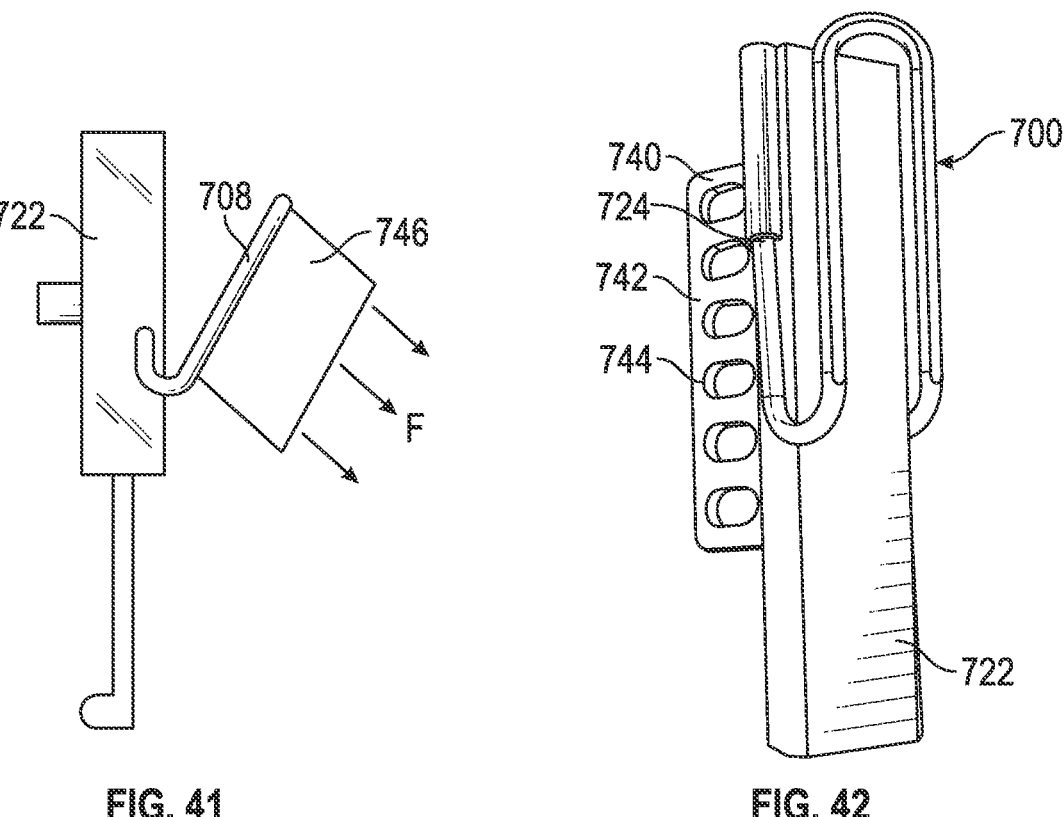
FIG. 41                                    FIG. 42

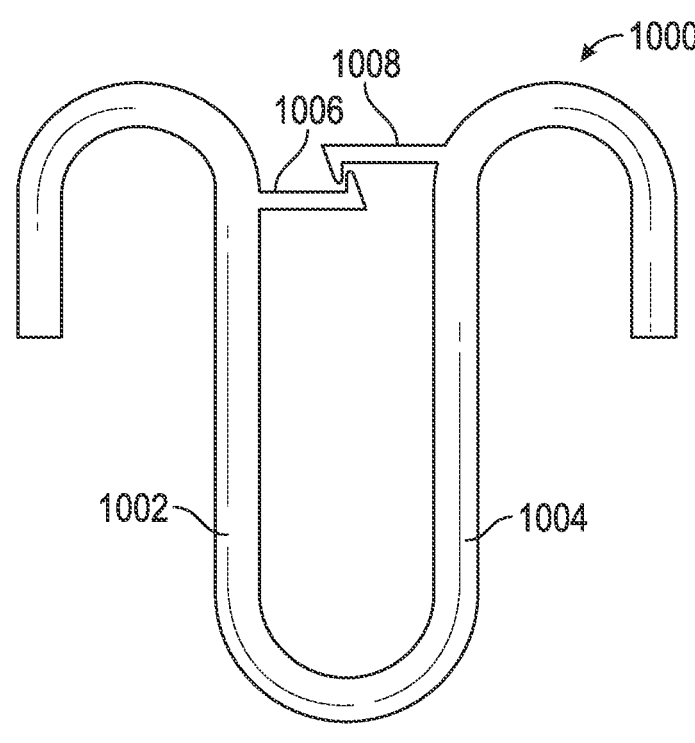
FIG. 49
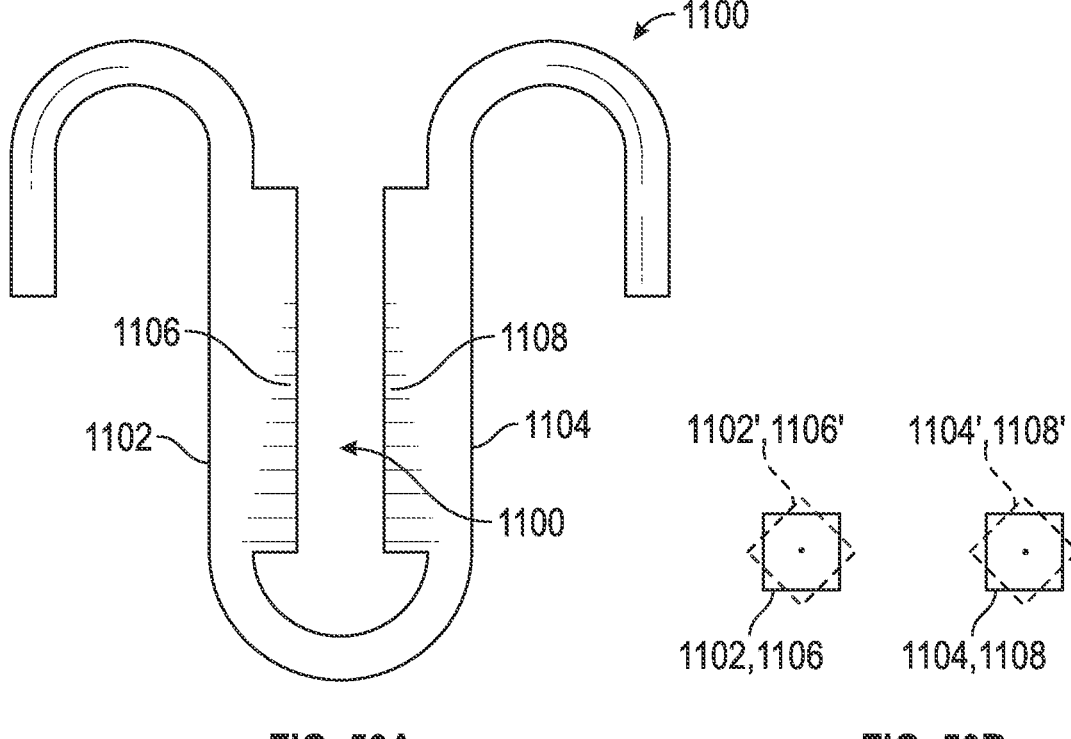
FIG. 50A                          FIG. 50B

PROSTHETIC HEART VALVE HAVING COMMISSURE SUPPORT ELEMENT

CROSS REFERENCE TO RELATED APPLICATION

The present application is a continuation of International Application No. PCT/US2019/061392, filed Nov. 14, 2019, which claims the benefit of U.S. Provisional Application No. 62/767,412, filed on Nov. 14, 2018, which is incorporated herein by reference in its entirety.

FIELD

The present application relates to prosthetic heart valves including clamps for clamping the leaflets of the prosthetic heart valve together to form commissures.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design consideration is attachment of the leaflets to the frame of the prosthetic valve to form commissures, which can be difficult and time-consuming, and which can increase the diameter of the prosthetic valve in the collapsed state. Accordingly, there is a need for improvements to devices and methods for securing leaflets together to form commissures in prosthetic heart valves.

SUMMARY

Certain embodiments of the disclosure concern prosthetic heart valves including commissure support elements such as commissure clamps that clamp the leaflets of the prosthetic valve together to form a commissure. In one representative embodiment, a prosthetic heart valve comprises an annular frame comprising a plurality of angled strut members, the frame being radially collapsible to a collapsed configuration and radially expandable to an expanded configuration, the frame having an inflow end and an outflow end. The prosthetic heart valve further comprises a leaflet structure positioned at least partially within the frame, the leaflet structure comprising a plurality of leaflets arranged to form a plurality of commissures. The frame includes a plurality of commissure support elements, each commissure support element being positioned at one of the commissures. Each of the commissure support elements comprising a coupling portion coupled to the frame and first and second members coupled to the coupling portion and extending in a direction toward the inflow end of the frame or toward the outflow end of the frame. The leaflets of each commissure are received between the first and second members of the respective commissure support element.

In any or all of the disclosed embodiments, the coupling portion comprises an annular collar portion.

In any or all of the disclosed embodiments, the prosthetic heart valve further comprises a plurality of axially extending posts coupled to an inner surface of the frame, and the collar portion of the commissure support element at each commissure is disposed around the post at the commissure.

In any or all of the disclosed embodiments, the first and second members are coupled together distally of the collar portion and define a leaflet-receiving space through which leaflets are received.

In any or all of the disclosed embodiments, the first and second members are coupled together radially inwardly of the post.

In any or all of the disclosed embodiments, the first and second members are spaced radially inwardly from the post, and leaflets of the commissures are sutured to the first and second members of the respective commissure support elements in a space between the post and the first and second members.

In any or all of the disclosed embodiments, the first and second members are coupled to the collar portion by curved members that curve in a direction of the outflow end of the frame.

In any or all of the disclosed embodiments, the collar portion comprises at least one protrusion configured to engage a corresponding recess in the post.

In any or all of the disclosed embodiments, each of the first and second members comprise at least one opening.

In any or all of the disclosed embodiments, the posts comprise recesses configured to receive the collar portions of the commissure support elements.

In any or all of the disclosed embodiments, the coupling portion is rectangular.

In any or all of the disclosed embodiments, the collar portion is a first collar portion, and the first and second members are coupled together radially outwardly of the post to form a second collar portion longitudinally spaced apart from the first collar portion.

In any or all of the disclosed embodiments, the first and second members of each commissure support element are clamping members rotatable away from the post to receive a leaflet.

In any or all of the disclosed embodiments, the posts comprise grooves configured to receive the first and second collar portions of the commissure support elements.

In any or all of the disclosed embodiments, the first and second collar portions are angled toward each other.

In any or all of the disclosed embodiments, each leaflet is folded to form a cuff that is circumferentially offset from the respective clamping member that clamps the leaflet against the frame.

In any or all of the disclosed embodiments, the cuff of each leaflet is configured to contact the frame to prevent rotation of the leaflet about the respective clamping member by which it is clamped against the frame during operation of the prosthetic heart valve.

In any or all of the disclosed embodiments, the cuffs comprise folded edges oriented radially inward toward a center of the prosthetic heart valve.

In any or all of the disclosed embodiments, the first and second collar portions of the commissure support element have a shape that conforms to a shape of the posts.

In any or all of the disclosed embodiments, the coupling portion comprises a first coupling member and a second coupling member configured to engage the frame.

In any or all of the disclosed embodiments, the prosthetic heart valve further comprises a plurality of axially extending posts coupled to an inner surface of the frame, and the first coupling member and the second coupling member are received in the post at the commissure.

In any or all of the disclosed embodiments, the post defines channels configured to receive the first coupling member and the second coupling member.

In any or all of the disclosed embodiments, the first and second members extend in a direction toward the outflow end of the frame.

In any or all of the disclosed embodiments, the first and second coupling members comprise projections configured to engage the post.

In any or all of the disclosed embodiments, the first member comprises a clasp configured to engage a clasp of the second member.

In any or all of the disclosed embodiments, the prosthetic heart valve further comprises suture extending between the first and second members to clamp the leaflets between the first and second members.

In any or all of the disclosed embodiments, the first and second members of the commissure support elements each comprise flexible tab portions resiliently engaging the leaflets at each respective commissure.

In any or all of the disclosed embodiments, the first and second members of the commissure support elements comprise projections that engage the leaflets of the respective commissure.

In any or all of the disclosed embodiments, the frame is a mechanically expandable frame and the posts comprise components of actuators configured to radially expand and collapse the frame. The collar portion of the commissure support element at each commissure is disposed around the actuator component at the commissure.

In another representative embodiment, a prosthetic heart valve comprises an annular frame including a plurality of angled strut members, the frame being radially collapsible to a collapsed configuration and radially expandable to an expanded configuration. The prosthetic heart valve further comprises a leaflet structure positioned at least partially within the frame, the leaflet structure comprising a plurality of leaflets arranged to form a plurality of commissures. The prosthetic heart valve further comprises a plurality of commissure clamps, each commissure clamp being positioned at one of the commissures, each of the commissure clamps comprising a wire form member curved to form a first collar portion and a second collar portion, the first and second collar portions being spaced apart from each other along a longitudinal axis of the prosthetic heart valve and interconnected by first and second clamping members formed by the wire form member and extending between the first and second collar portions. At each respective commissure, one leaflet of the commissure is clamped against the frame by the first clamp member, and the other leaflet of the commissure is clamped against the frame by the second clamp member.

In any or all of the disclosed embodiments, the prosthetic heart valve further comprises a plurality of axially extending posts coupled to an inner surface of the frame, and the first and second collar portions of the commissure clamp at each commissure are disposed around the post at the commissure.

In any or all of the disclosed embodiments, the frame is a mechanically expandable frame and the posts comprise components of actuators configured to radially expand and compress the frame. The first and second collar portions of the commissure clamp at each commissure are disposed around the actuator component at the commissure.

In any or all of the disclosed embodiments, the first and second clamping members of each commissure clamp are rotatable away from the actuator component to receive a leaflet.

In any or all of the disclosed embodiments, the posts comprise grooves configured to receive the first and second collar portions of the commissure clamps.

In any or all of the disclosed embodiments, the first and second collar portions are angled toward each other.

In any or all of the disclosed embodiments, each leaflet is folded to form a cuff that is circumferentially offset from the respective clamping member that clamps the leaflet against the frame.

In any or all of the disclosed embodiments, the cuff of each leaflet is configured to contact the frame to prevent rotation of the leaflet about the respective clamping member by which it is clamped against the frame during operation of the prosthetic heart valve.

In any or all of the disclosed embodiments, the cuffs comprise folded edges oriented radially inward toward a center of the prosthetic heart valve.

In any or all of the disclosed embodiments, the collar portions of the commissure clamps have a shape that conforms to a shape of the posts.

In another representative embodiment, a prosthetic heart valve comprises an annular mechanically-expandable frame comprising a plurality of angled strut members. The frame comprises a plurality of actuator components configured to radially collapse the frame to a collapsed configuration and radially expand the frame to an expanded configuration, and has an inflow end and an outflow end. The prosthetic heart valve further comprises a leaflet structure positioned at least partially within the frame, the leaflet structure comprising a plurality of leaflets arranged to form a plurality of commissures. The prosthetic heart valve further comprises a plurality of commissure support elements, each commissure support element being positioned at one of the commissures, each of the commissure support elements comprising a coupling portion coupled to an actuator of the frame and first and second members coupled to the coupling portion and extending in a direction along the longitudinal axis of the frame. The leaflets of each commissure are received between the first and second members of the respective commissure support element. The first and second members are spaced apart along at least a portion of their length and define a leaflet-receiving space through which leaflets are received. The first and second members are coupled together at a location spaced apart from the collar portion in a direction toward the inflow end of the frame or toward the outflow end of the frame.

In any or all of the disclosed embodiments, the first and second members are coupled together radially inwardly of the actuator.

In any or all of the disclosed embodiments, the coupling portion is a first coupling portion, and the first and second members are coupled together radially outwardly of the post to form a second collar portion longitudinally spaced apart from the first collar portion.

The foregoing and other objects, features, and advantages of the disclosed technology will become more apparent from the following detailed description, which proceeds with reference to the accompanying figures.

BRIEF DESCRIPTION OF THE DRAWINGS

FIG. 6 is a perspective view of another embodiment of a commissure clamp formed from a wire member.

FIGS. 7-9 illustrate the commissure clamp of FIG. 6 positioned on an actuator component of a mechanically-expandable prosthetic heart valve.

FIG. 10 is a rear perspective view of an actuator component.

FIG. 11 is a front elevation view of the commissure clamp of FIG. 6 positioned on an actuator component.

FIG. 20A is a perspective view of a commissure support element including a collar portion and two members extending from the collar portion to define a leaflet-receiving space, according to one embodiment.

FIG. 20B is a perspective view of another embodiment of a commissure support element.

FIG. 21 is a perspective view of an actuator component.

FIGS. 40 and 41 are side elevation views schematically illustrating forces developed by leaflets coupled to the commissure support element of FIG. 38 at various angles.

FIG. 42 is a perspective view of an assembly including the commissure support element of FIG. 38 and a commissure plate coupled to an actuator component.

FIG. 49 is a front elevation view of a commissure support element in which the first and second members include complementary clasp members, according to one embodiment.

FIG. 50A is a front elevation view of a commissure support element in which the first and second members include flexible leaflet-engaging portions, according to one embodiment.

FIG. 50B is a cross-sectional top plan view schematically illustrating rotation of the flexible leaflet-engaging portions of FIG. 50A.

DETAILED DESCRIPTION

The present disclosure pertains to prosthetic heart valves including commissure support elements, such as commissure clamps, for clamping the edges or tab portions of two adjacent leaflets together to form a commissure. In certain embodiments, the commissure clamps can comprise, or can be made from, wire form members that are bent or curved to assume the selected shape. In the case of mechanically-expandable prosthetic heart valves, the wire form commissure clamps can be positioned around actuator assemblies or components of the frame. The commissure clamps can be elastic structures, and can clamp the leaflets together, as well as against the actuator component and/or other portions of the frame. Due to the relatively small diameter of the wire members, the commissure clamps can clamp the leaflets together without significantly increasing the overall crimp profile of the valve. In embodiments in which the commissure clamps are elastically deformable, the leaflets and commissure clamps can be assembled together, and then the commissure clamps can be temporarily elastically deformed for positioning on the actuator components of the prosthetic valve frame.

In certain embodiments the commissure support elements can comprise a coupling portion configured to be coupled to a post, such as an actuator component of a mechanically-expandable valve, and a pair of members extending from the post along the longitudinal axis of the prosthetic valve. The members can be spaced apart from each other, and can define a leaflet-receiving region configured to receive the leaflets of a commissure. The members can be coupled together at a location offset from the coupling portion in the inflow direction or the outflow direction. In certain embodiments, the coupling portion can comprise a collar portion that is disposed around the actuator component. In certain embodiments, the coupling portion comprises a pair of coupling members that can be received in corresponding channels or openings defined in the actuator component. The commissure support elements can be configured to reduce the stresses on the leaflets where the leaflets are attached to the commissure support elements, while also maintaining a low crimp profile of the collapsed prosthetic valve.

Figure 1:
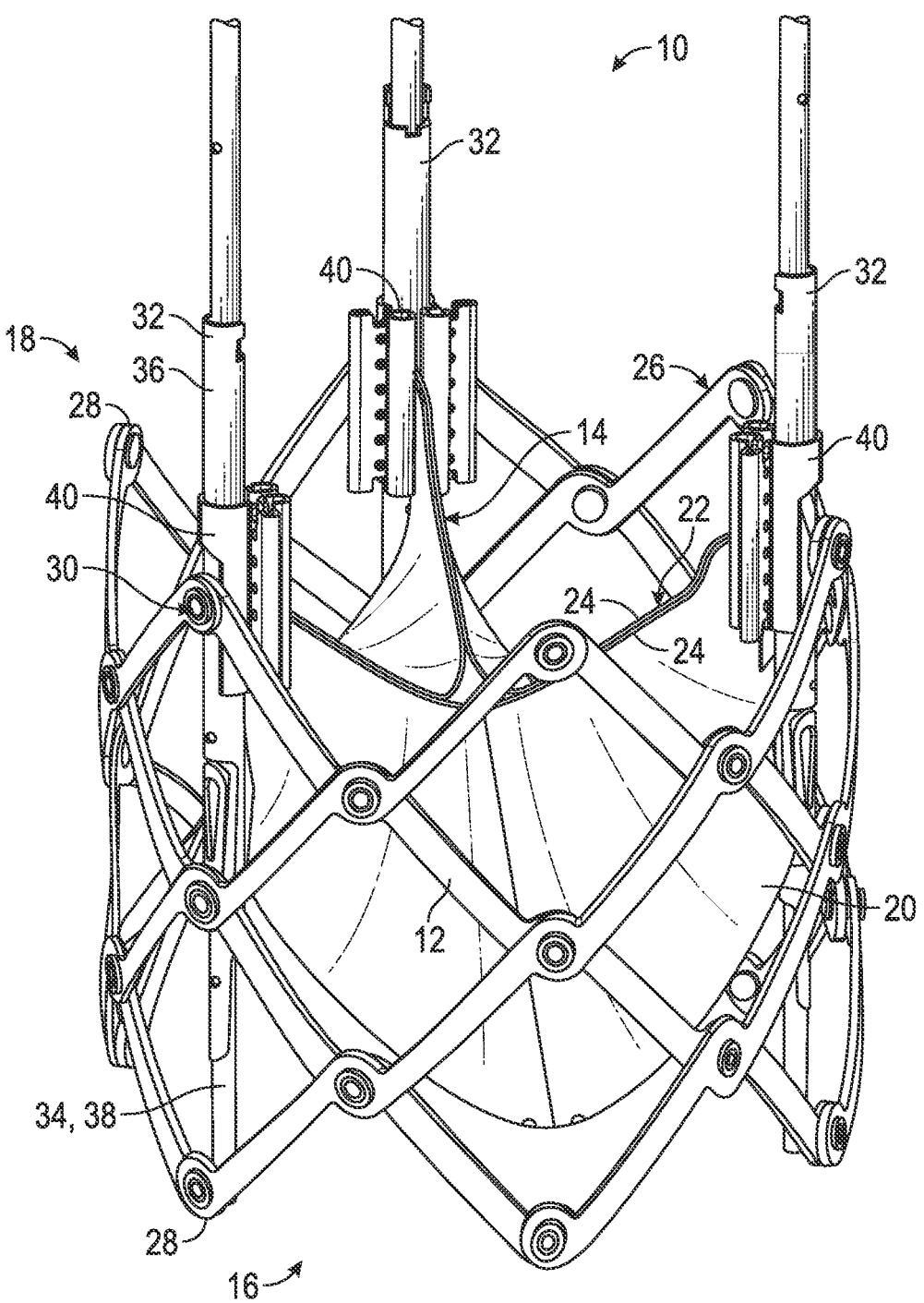
FIG. 1 is a perspective view of a mechanically-expandable prosthetic heart valve, according to one embodiment.

FIG. 1 illustrates a mechanically-expandable prosthetic heart valve 10, according to one embodiment. The prosthetic valve 10 can include an annular stent or frame 12, and a leaflet structure 14 situated within and coupled to the frame 12. The frame 12 can include an inflow end 16 and an outflow end 18. The leaflet structure can comprise a plurality of leaflets 20, such as three leaflets arranged to collapse in a tricuspid arrangement similar to the aortic valve, such that the leaflets form commissures 22 where respective outflow edge portions 24 of the leaflets contact each other. Alternatively, the prosthetic valve can include two leaflets 20 configured to collapse in a bicuspid arrangement similar to the mitral valve, or more than three leaflets, depending upon the particular application.

The frame 12 can include a plurality of interconnected lattice struts 26 arranged in a lattice-type pattern and forming a plurality of apices 28 at the outflow end 18 of the prosthetic valve. The struts 26 can also form similar apices 28 at the inflow end 16 of the prosthetic valve. The lattice struts 26 can be pivotably coupled to one another by hinges 30 located where the struts overlap each other, and also at the apices 28. The hinges 30 can allow the struts 26 to pivot relative to one another as the frame 12 is expanded or contracted, such as during assembly, preparation, or implantation of the prosthetic valve 10. The hinges 30 can comprise rivets or pins that extend through apertures formed in the struts 26 at the locations where the struts overlap each other. Additional details regarding the frame 12 and devices and techniques for radially expanding and collapsing the frame can be found in U.S. Publication No. 2018/0153689, which is incorporated herein by reference.

As illustrated in FIG. 1, the frame 12 can comprise a plurality of actuator components 32 that can also function as release-and-locking units (also referred to as locking assemblies) configured to radially expand and contract the frame. In the illustrated configuration, the frame 12 can comprise three actuator components 32 configured as posts and coupled to the frame 12 at circumferentially spaced locations, although the frame may include more or fewer actuator components depending upon the particular application. Each of the actuator components 32 generally can comprise an inner member 34, such as an inner tubular member, and an outer member 36, such as an outer tubular member concentrically disposed about the inner member 34. The inner members 34 and the outer members 36 can be moveable longitudinally relative to each other in a telescoping manner to radially expand and contract the frame 12, as further described in U.S. Publication No. 2018/0153689 incorporated by reference above.

In the illustrated configuration, the inner members 34 can have distal end portions 38 coupled to the inflow end 16 of the frame 12 (e.g., with a coupling element such as a pin member). In the illustrated embodiment, each of the inner members 34 are coupled to the frame at respective apices 28 at the inflow end 16 of the frame. The outer members 36 can be coupled to apices 28 at the outflow end 18 of the frame 12 at, for example, a mid-portion of the outer member, as shown in FIG. 1, or at a proximal end portion of the outer member, as desired.

The inner member 34 and the outer member 36 can telescope relative to each other between a fully contracted state (corresponding to a fully radially expanded state of the prosthetic valve) and a fully extended state (corresponding to a fully radially compressed state of the prosthetic valve). In the fully extended state, the inner member 34 is fully extended from the outer member 36. In this manner, the actuator components 32 allow the prosthetic valve to be fully expanded or partially expanded to different diameters and retain the prosthetic valve in the partially or fully expanded state.

In alternative embodiments, the actuator components 32 can be screw actuators configured to radially expand and compress the frame 12 by rotation of one of the components of the actuators. For example, the inner members 34 can be configured as screws having external threads that engage internal threads of corresponding outer components. Further details regarding screw actuators are disclosed in U.S. Publication No. 2018/0153689.

Referring to FIG. 1, the prosthetic valve 10 can include a plurality of commissure support elements configured as commissure clasps or clamps 40. In the illustrated configuration, the prosthetic valve includes a commissure clamp 40 positioned at each commissure 22 and configured to grip the leaflets 20 of the commissure at a location spaced radially inwardly of the frame 12.

Figure 2:
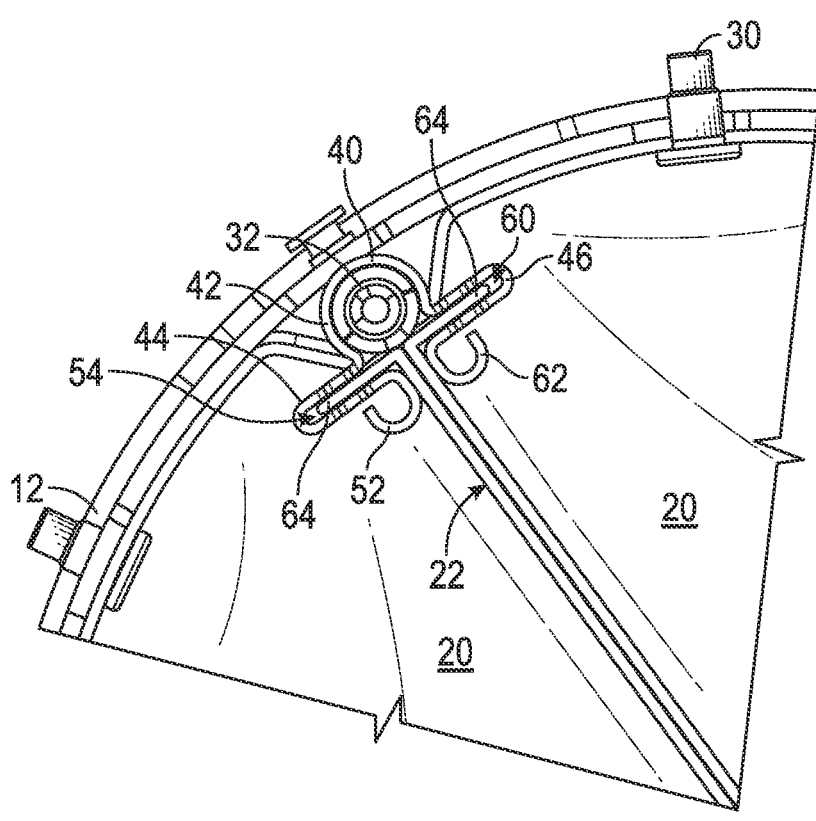
FIG. 2 is a top plan view illustrating a portion of the prosthetic heart valve of FIG. 1.
Figure 3:
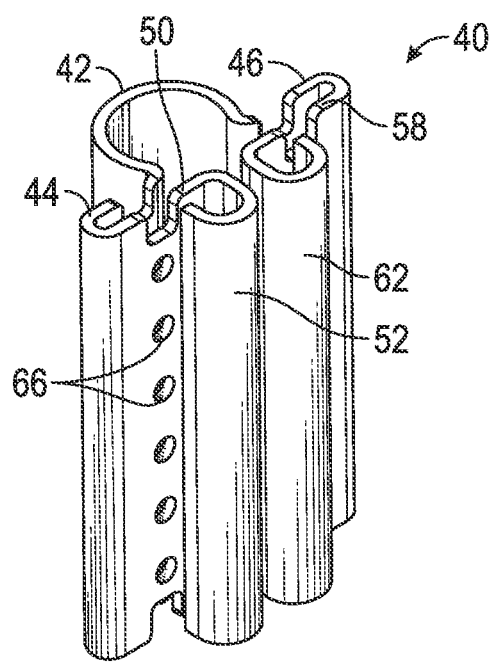
FIG. 3 is a perspective view of a commissure clamp, according to one embodiment.
Figure 4:
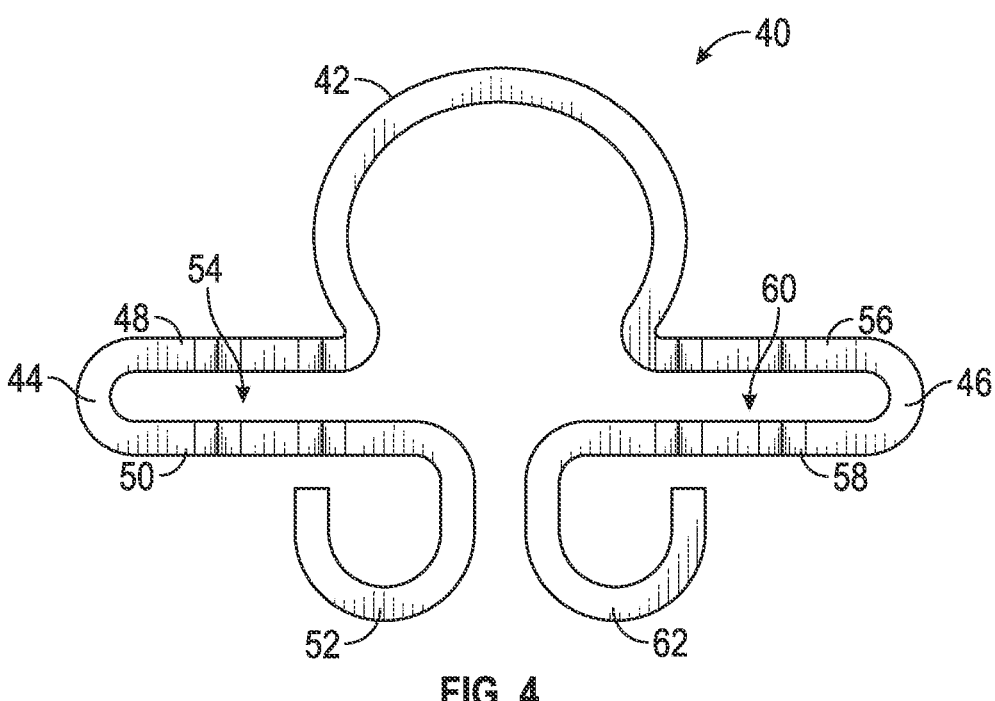
FIG. 4 is a top plan view of the commissure clamp of FIG. 3.

FIGS. 2-4 illustrate a representative commissure clamp 40 in greater detail. The commissure clamp 40 can include a main portion or coupling portion 42 configured as a cylindrically-shaped recessed portion or collar, and first and second clamp members 44, 46 extending curvilinearly from opposite sides of the coupling portion 40. As best shown in FIG. 4, the first clamp member 44 can include a first portion 48 extending away from the coupling portion 42. The clamp member 44 can be curved (e.g., by 180°) such that a second portion 50 extends from the first portion 48 parallel to and spaced apart from the first portion 48 in a direction back toward the coupling portion 42. A third portion 52 can extend from the second portion 50, and can curve around (e.g., by 180°) such that an end portion of the third portion 52 is adjacent a mid-portion of the second portion 50. The first and second portions 48, 50 can define a leaflet-receiving space 54 therebetween. The second clamp member 46 can be symmetrical with the first member 44, and can include first and second portions 56, 58 defining a leaflet-receiving space 60 opposite the leaflet-receiving space 54 and in communication with the leaflet-receiving space 54. A curved third portion 62 can extend from the second portion 58 similar to the portion 52 of the first member 44. As shown in FIG. 3, the inward-facing surfaces of the second portions 50, 58 can comprise openings 66.

Referring again to FIG. 1, the commissure clamps 40 can be situated on the actuator components 32 such that the outer members 36 are received in the coupling portions 42 of the commissure clamps, and such that the leaflet-receiving spaces 54 and 60 extend at an angle to the commissure 22 (e.g., at an angle of 90°). The coupling portion 42 can be sized and shaped to frictionally engage and/or clamp onto the outer surface of the outer member 36 of the actuator component 32 so as to secure the commissure clamp 40 to the outer member 36. In lieu of or in addition to frictional or clamping forces, the coupling portion 42 can be welded to the outer member 36, or secured to the outer member 36 using an adhesive, sutures and/or mechanical fasteners.

As shown in FIGS. 1 and 2, commissure tabs 64 (FIG. 2) of the leaflets 20 can be inserted into the leaflet-receiving spaces 54, 60 (FIG. 2) of the commissure clamps 40 at each coinsure. For example, the commissure tab 64 of one leaflet 20 can be folded around the third portion 52 and inserted into the leaflet-receiving space 54 such that a portion of the commissure tab extends radially between the third portions 52 and 62 of the members 44 and 46, and the portion of the commissure tab in the leaflet-receiving space 54 extends circumferentially along the frame. The commissure tab 64 of the other leaflet 20 can be folded and inserted into the leaflet-receiving space 60 in a similar manner. In certain configurations, the leaflets 20 can be sutured to the commissure clamps 40 through the openings 66 (FIG. 3).

The curved third portions 52, 62 of the first and second clamp members can cooperate to grip the leaflets 20 of each commissure 22 at a location that is offset radially inwardly from the strut members of the frame 12. In this manner, the leaflets 20 can articulate about axes offset from the frame 12 as they coapt and move away from each other during valve operation. For example, in the illustrated configuration the leaflets 20 can articulate about the third portions 52, 62 of the first and second clamp members 44, 46. In certain configurations, the portions 52, 62 can be smooth, and can have relatively large radii configured to reduce stress and/or damage to the leaflets where the leaflets contact the members 44, 46 during valve operation.

Figure 5:
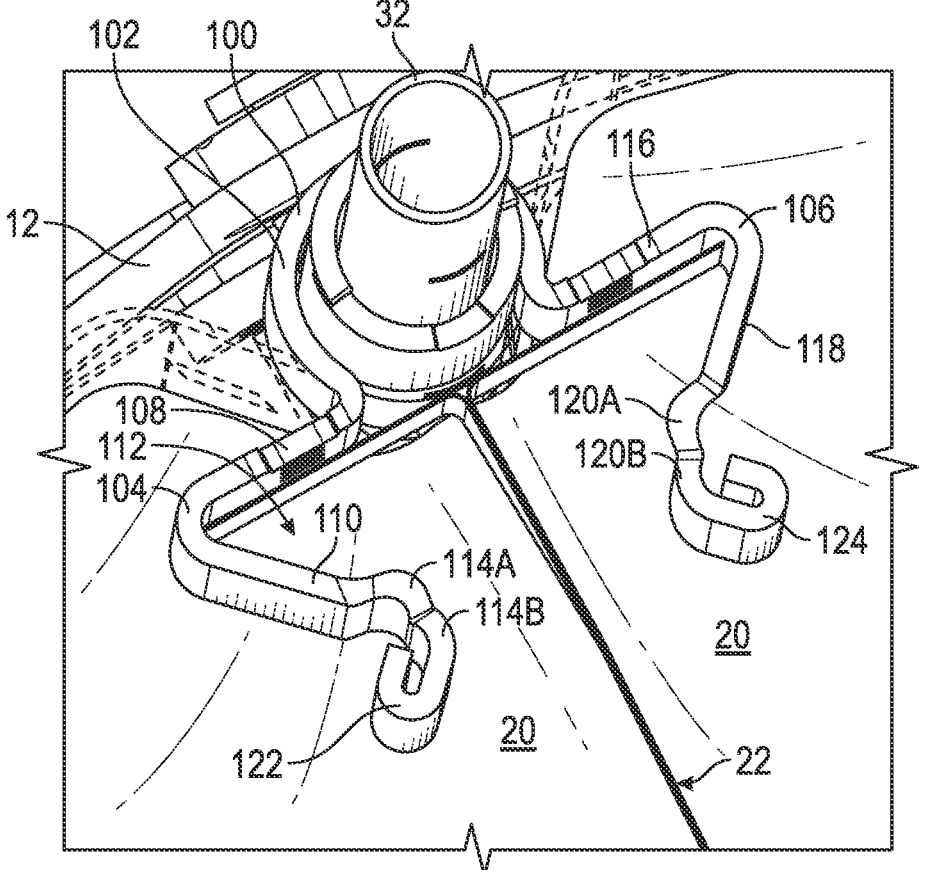
FIG. 5 is a perspective view illustrating a portion of the prosthetic heart valve of FIG. 1 including another embodiment of a commissure clamp.

FIG. 5 illustrates another embodiment of a commissure clamp 100 that can be used in combination with the prosthetic valve 10 of FIG. 1. In FIG. 5, the commissure clamp 100 is shown in an open configuration prior to crimping or closing of the clamping arms to clamp the leaflets 20. The commissure clamp 100 can include a main portion configured as a coupling portion 102 defining a cylindrically-shaped recess that is shaped to be placed around an actuator component. The commissure clamp can further comprise first and second clamp members 104, 106 extending from the coupling portion 102. The first clamp member 104 can include a first portion 108 extending outwardly from the coupling portion 102, and a second portion 110 extending at an angle to the first portion 108 such that the first and second portions 108, 110 define a leaflet-receiving space 112. The second portion 110 can include one or more curved portions configured as leaflet-engaging portions 114. In the illustrated embodiment, the first clamp member 104 includes two leaflet-engaging portions 114A and 114B, wherein the leaflet-engaging portion 114B is offset from the leaflet-engaging portion 114A in a direction radially inward toward the center of the prosthetic valve in the position illustrated in FIG. 5.

The second clamp member 106 can be configured similar to the first clamp member 104, with a first portion 116 extending from the coupling portion 102 in the opposite direction from the first portion 108 of the first clamp member 104. The second clamp member 106 can further include a second portion 118 extending at an angle to the first portion 116. The second portion 118 can include two curved leaflet-engaging portions 120A and 120B opposing the leaflet-engaging portions 114A, 114B of the first member 104. In the configuration illustrated in FIG. 5, the leaflet-engaging portion 120B can be offset from the leaflet-engaging portion 120A in a direction radially inward toward the center of the prosthetic valve, similar to the leaflet-engaging portion 114B.

The second portions 110, 118 of the first and second clamp members 104, 106 can be configured to clamp the leaflets 20 (or commissure tabs of the leaflets) when the leaflets are inserted between the first and second clamp members. In certain embodiments, the second portions 110 and 118 of the respective clamp members 104 and 106 can be crimped from the open position shown in FIG. 5 to a closed position wherein the portion 110 is parallel to the portion 108 and the portion 118 is parallel to the portion 116, similar to the embodiment of FIG. 4. In the closed configuration, the leaflet-engaging portion 114A can clamp the leaflet 20 on the left side of FIG. 5 against the portion 108, and the leaflet-engaging portion 120A can clamp the leaflet 20 on the right side of FIG. 5 against the portion 116.

Meanwhile, the leaflets 20 can also be clamped or pressed together between the leaflet-engaging portions 114B and 120B, and/or between the curved end portions 122 and 124 of the respective members 104 and 106. In this manner, the leaflets 20 can articulate about axes adjacent the end portions 122 and 124 spaced radially inwardly from the frame 12.

In other embodiments, the clamp members 104 and 106 can remain in the configuration illustrated in FIG. 5, and the leaflet-engaging portions 114A and 120A can cooperate to clamp the leaflets 20 at a first location, and the leaflet-engaging portions 114B and 120B can clamp the leaflets at a second location adjacent the first location. In this manner, the leaflets 20 can articulate about axes adjacent the leaflet-engaging portions 114B and 120B, and offset radially inwardly from the frame 12.

Additionally, in certain configurations, clamping the leaflets at multiple locations, such as between the leaflet-engaging portion 114A and the portion 108 on the left side of FIG. 5, between the leaflet-engaging portion 120A and the portion 116 on the right side of FIG. 5, between the portions 114B and 120B, and/or between the end portions 122 and 124, can increase the overall clamping force of the clamp 100 against the leaflets. In some embodiments, the leaflet-engaging portions 114A and 120A can also provide elastic strain-recovery shape-maintenance functionality, which is described in greater detail in U.S. application Ser. No. 15/978,459, filed on May 14, 2018, which is incorporated herein by reference.

Figures 6, 7:
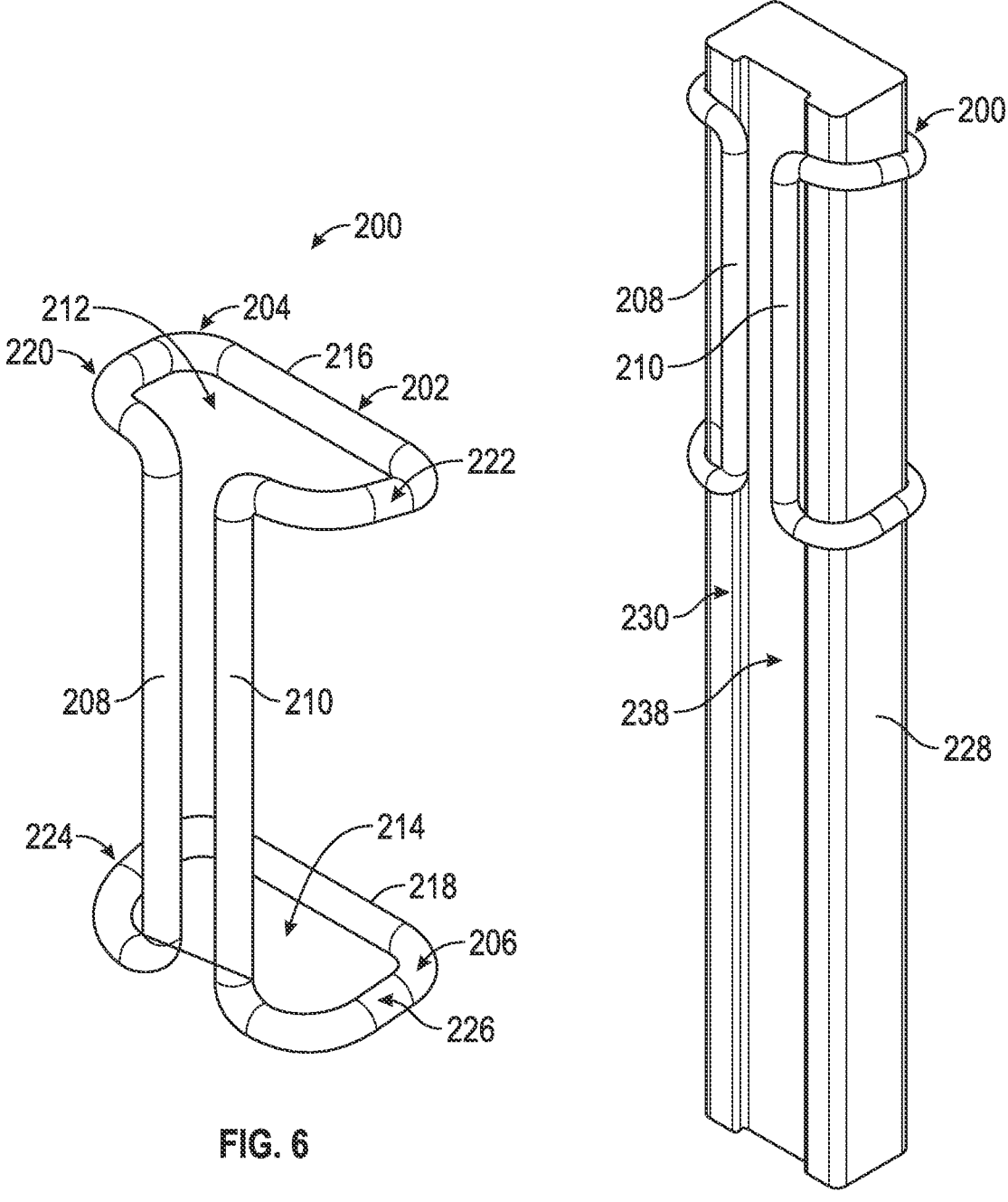

FIG. 6 illustrates another embodiment of a commissure clamp 200 (also referred to as a commissure support element) comprising a relatively small diameter, wire-form body or member 202. In certain embodiments, the member 202 can be a thin, flexible, wire or rod with a single or multiple layers of the same or different materials, and can be bent or formed into a variety of shapes. For example, in the configuration illustrated in FIG. 6, the wire member 202 is bent or formed such that the clamp comprises a first ring, coupling portion, or collar portion 204, and a second coupling portion or collar portion 206. The first and second collar portions 204, 206 can be axially spaced apart from each other by a first clamping member, or connecting member, 208 and a second clamping member, or connecting member, 210, which can be formed from the wire member 202, and can extend between and interconnect the collar portions 204 and 206. The first collar portion 204 can at least partially enclose a space or opening 212, and the second collar portion 206 can at least partially enclose a space or opening 214.

In the illustrated embodiment, the first collar portion 204 can comprise a relatively straight rear or radially outward portion 216, and the second collar portion 206 can comprise a corresponding straight rear portion 218. The rear portion 216 can be coupled to the clamp members 208 and 210 by respective radially extending side portions 220 and 222, which can be curved or u-shaped in the plane of the collar portion 204. The portions 220 and 222 can offset the rear portion 216 away from the clamp members 208 and 210 in, for example, the radially outward direction when the commissure clamp is positioned in a frame of a prosthetic valve. The second collar portion 206 can comprise portions 224 and 226 configured similarly to the portions 220 and 222.

The wire body 202 can be formed from any of a variety of elastically deformable materials and/or plastically deformable materials such as metals including nitinol, stainless steel, cobalt-chromium, etc., or polymeric materials. Exemplary polymeric materials can include ultra-high-molecular-weight polyethylene (UHMWPE) (e.g., Dyneema®), high-molecular-weight polyethylene (HMWPE), or polyether ether ketone (PEEK), polytetrafluoroethylene (PTFE), expanded polytetrafluoroethylene (ePTFE), ethylene tetrafluoroethylene (ETFE), nylon, polyethylene, polyether block amide (e.g., Pebax), and/or combinations of any of the above. In some embodiments, the wire body can comprise multiple layers such as, for example, an inner metal layer and one or more polymeric outer layers.

In particular embodiments, a clamp 200 (and the other embodiments of clamps disclosed herein) can be formed by bending a piece of wire (e.g., a straight piece of wire) into the shape shown in FIG. 6 and securing the free ends of the wire together, such as by welding. In alternative embodiments, other techniques and/or methods can be used to form a clamp 200 (and the other embodiments of clamps disclosed herein). For example, a clamp can be formed by molding (e.g., injection molding), machining (e.g., laser cutting), or 3D printing.

FIGS. 7-10 are various views illustrating the commissure clamp 200 situated on an actuator component 228. The actuator component 228 can be, for example, the outer member of an actuator of a mechanically-expandable prosthetic heart valve, similar to the outer members 36 of the actuator components 32 of the prosthetic valve 10 of FIG. 1. In the illustrated embodiment, the actuator component 228 can have a rectangular cross-section, although in other embodiments the actuator component may have a round cross-section, or a cross-section having any other selected shape. Desirably, the collar portions 204, 206 can be shaped to correspond to the cross-sectional shape of the actuator component taken in a plane perpendicular to the longitudinal axis 237 of the actuator component. The commissure clamp 200 can be positioned on the actuator component 228 such that the clamping members 208 and 210 are situated against a radially inward-facing surface 230 of the actuator component 228, and the rear portions 216 and 218 are disposed around a radially outward-facing surface 232 (FIG. 8) of the actuator component.

Referring to FIG. 10, in certain embodiments the actuator components 228 can comprise grooves or channels 234 and 236 configured to receive the portions 216 and 218 of the commissure clamp. Referring to FIG. 9, in certain embodiments the portions 220, 222, 224, and/or 226 can be angled with respect to the longitudinal axis 237 of the actuator component 228. For example, FIG. 9 illustrates the portions 222 and 226 angled toward each other. The portions 220-226 can be angled from 5° to 60°, depending upon the particular application. In some embodiments, the radially inward surface 230 of the actuator component 228 can define an axially-extending groove or channel 238.

In certain embodiments, the leaflets of a commissure can be assembled together with the commissure clamps prior to positioning the commissure clamps in a valve frame. For example, in some embodiments the leaflets, or tab portions thereof, can be folded around and optionally attached (e.g., sutured) to the clamp members 208 and 210. In embodiments in which the wire member 202 comprises a flexible or elastically deformable material, the clamping members 208 and 210 can be "opened" by rotating or moving the clamping members 208 and 210 apart to increase the spacing between them, as indicated by the double-headed arrows in FIG. 11. Thus, the assembled commissure clamp and leaflets can be coupled to the frame by opening the clamp members 208 and 210 in the manner shown in FIG. 11, and situating the commissure clamp 200 around the actuator component 228.

The commissure clamp 200 is shown positioned around the actuator component 228 in FIG. 11 without the leaflets for purposes of illustration.

Figure 12:
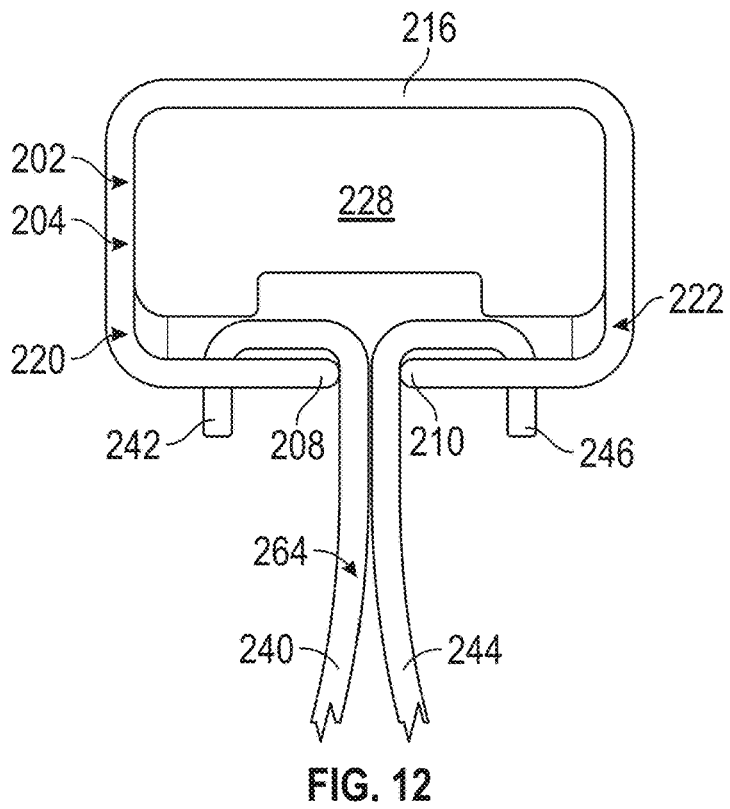
FIG. 12 is a top plan view of a portion of a mechanically-expandable prosthetic heart valve illustrating a commissure formed using the commissure clamp of FIG. 6.

For example, FIG. 12 illustrates a portion of an assembled commissure 264 in which a tab portion 242 of a leaflet 240 is folded around the clamping member 208, and clamped between the clamping member 208 and the actuator component 228. On the opposite side, a tab portion 246 of a leaflet 244 is folded around the clamping member 210 and clamped against the actuator component member 228 by the clamping member 210. In certain embodiments, the non-deformed or natural size of the collar portions 204 and 206 can be less than the diameter or thickness of the actuator component 228 such that the collar portions are in an expanded state when placed around the actuator component, thereby causing the members 208 and 210 to apply clamping force to the leaflets 240 and 244. Because the clamping members 208 and 210 are configured to lie against the actuator component 228 and do not extend into the lumen of the prosthetic valve, the commissure clamp 200 can provide a relatively low-profile leaflet attachment solution that does not significantly increase the crimp profile of the valve, and which is relatively easy to assemble. In other embodiments, the commissure clamp 200 can be placed around the actuator component 228 first, followed by insertion of the leaflets 240 and 244 between the respective clamp members and the actuator component.

Figure 13:
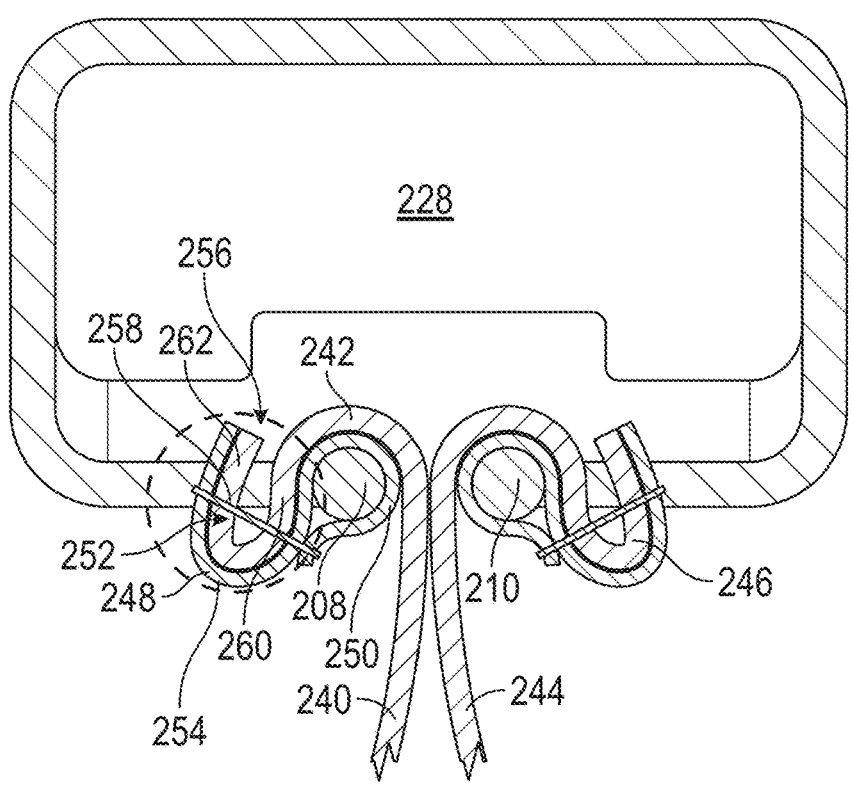
FIG. 13 is a cross-sectional top plan view of a portion of a mechanically-expandable prosthetic heart valve illustrating a commissure formed using the commissure clamp of FIG. 6, and in which the leaflets are folded to form cuffs.

In certain embodiments, the tab portions of the leaflets can be folded around or beside the clamping members of the commissure clamp to stabilize the commissure and prevent rotation of the leaflets during valve operation. For example, FIG. 13 illustrates an embodiment in which a reinforcing member configured as a fabric strip 248 is wrapped around the clamping member 208 and forms a loop 250. The fabric strip 248 can extend from the loop 250, and can be positioned on or around the radially inward-facing surface of the leaflet tab 242. The leaflet tab 242 can be folded on itself to form a cuff 252 having a first layer 260 and a second layer 262. More particularly, the cuff 252 can be folded about a fold line extending into the plane of the page in FIG. 13 such that a folded edge 254 of the cuff 252 can be oriented radially inwardly generally toward the center of the prosthetic valve, and the open side or fore edge 256 of the cuff can be oriented radially outward toward the actuator component 228. The construction can be sutured together with suture 258. The suture 258 can secure the fabric loop 250 around the clamping member 208. The suture 258 can also extend through both layers 260 and 262 of the cuff 252, and both corresponding layers of the fabric strip 248 disposed around the cuff 252. In this manner, the cuff 252, and more particularly the fabric strip 248 and the layer 262 of the leaflet tab, can abut or bear against the actuator component member 228, and can resist rotation and/or sliding of the leaflet 240 around the clamping member 208 as the leaflet opens and closes during valve operation. The fore edge 256 of the cuff can be open, as illustrated in FIG. 13, or may be closed, depending upon the particular application. A similar construction can be formed around the clamping member 210 with a reinforcing member, suture, and the tab portion 246 of the leaflet 244.

Figures 14, 15, 16:
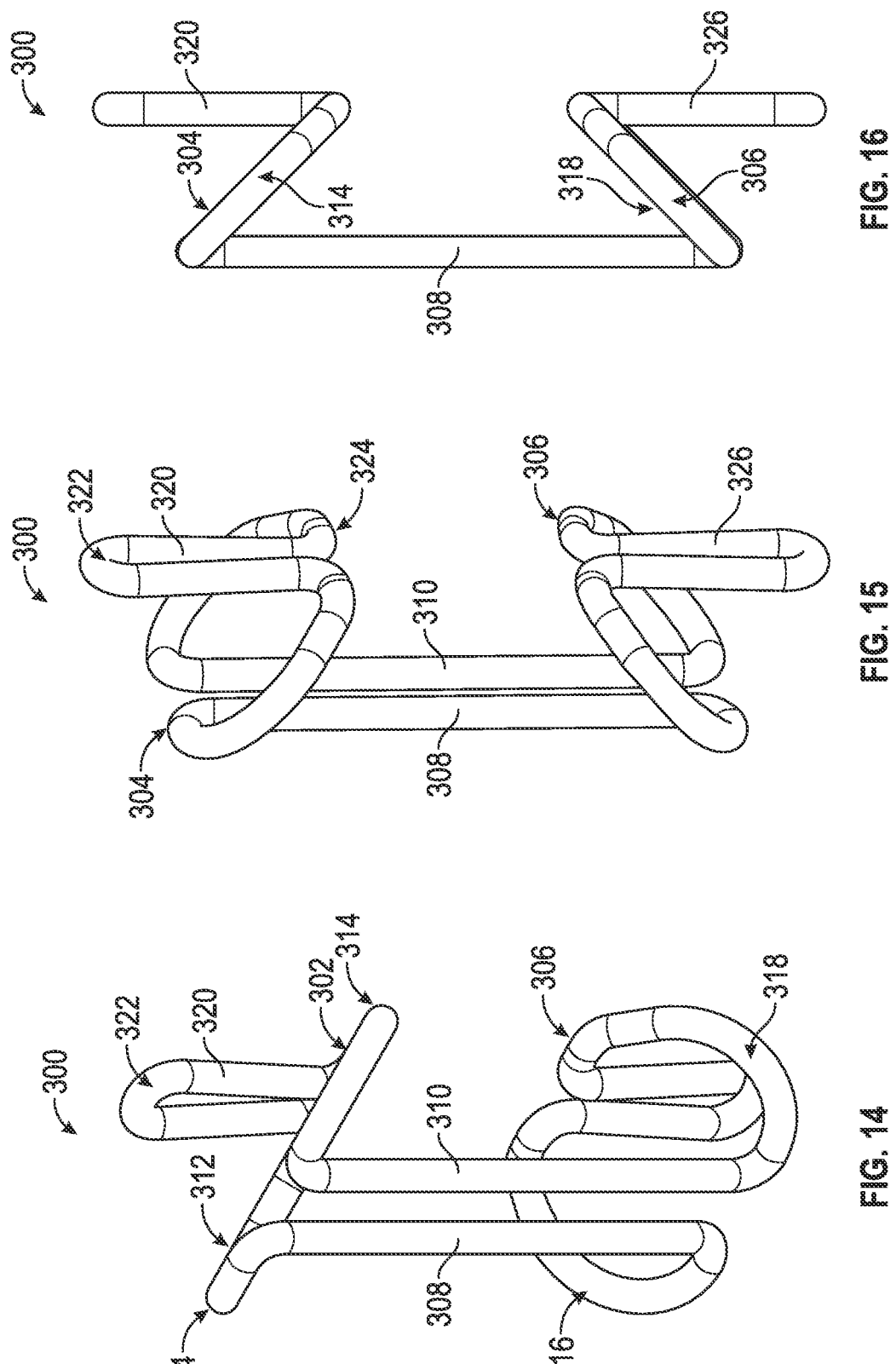
FIGS. 14-16 illustrate another embodiment of a commissure clamp.

FIGS. 14-16 illustrate another embodiment of a commissure clamp 300. The commissure clamp 300 can be formed from a relatively thin, wire-form body or member 302, similar to the embodiment of FIG. 6. The wire member 302 can be bent or formed such that the clamp 300 comprises a first coupling portion or collar portion 304, a second coupling portion or collar portion 306. First and second clamping members, or connecting members, 308 and 310 can extend between and interconnect the collar portions 304 and 306. Portions 312 and 314 of the first collar portion 304 can be curved, and angled downwardly toward the second collar portion 306. In the illustrated embodiment, portions 316 and 318 of the second collar portion 306 can be curved, and can be angled upwardly toward the first collar portion 304. With reference to FIG. 15, at the rear of the collar portion 304 opposite the clamping members 308 and 310, the wire member 302 can be bent to form a loop 320. The loop 320 can comprise a closed end portion 322 oriented upwardly in the figure, and an open end portion 324 facing downwardly toward the second collar portion 306. The wire member 302 can be bent to form a similar loop 326 at the rear of the second collar portion 306 oriented in the opposite direction from the loop 320.

Figures 17, 18, 19:
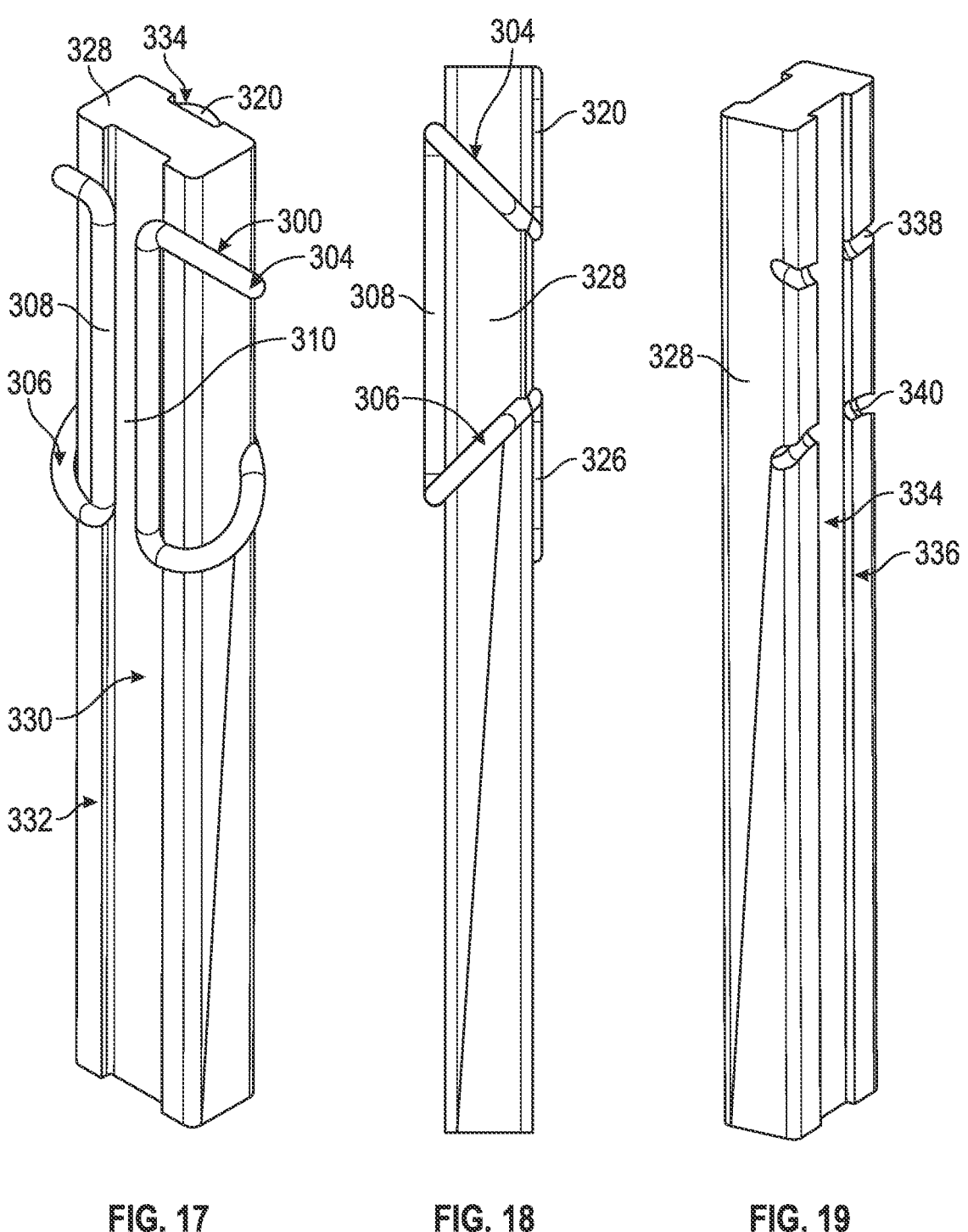
FIGS. 17 and 18 illustrate the commissure clamp of FIG. 14 positioned on an actuator component of a mechanically-expandable prosthetic heart valve.
FIG. 19 is a rear perspective view of the actuator component of FIGS. 17 and 18.

FIGS. 17 and 18 illustrate the commissure clamp 300 positioned on an actuator component 328 of, for example, a mechanically-expandable valve similar to the valve 10 of FIG. 1. Referring to FIGS. 17 and 19, in certain embodiments the actuator component 328 can comprise a channel or groove 330 in its radially-inward surface 332, and/or a groove 334 in its radially-outward surface 336. The grooves 330 and 334 can extend axially along the actuator component 328. Referring to FIG. 19, the radially-outward surface 336 can also comprise channels or grooves 338 and 340 extending perpendicular to the groove 334. When the commissure clamp 300 is disposed on the actuator component 328, the loops 320 and 326 can be received in the groove 334. The portions 312 and 314 of the first collar portion 304 can be received in the grooves 338, and the portions 316 and 318 of the collar portion 306 can be received in the grooves 340. The grooves on both sides of the actuator component 328 help align the commissure clamp at its proper location on the actuator component during assembly, assist in retaining the commissure clamp in place on the actuator component, and minimize the extent that portions of the clamp extend from the actuator component in a radial direction so as to further minimize the crimped profile of the prosthetic valve.

The clamping members 308 and 310 can be movable between an open position and a closed position in order to position the commissure clamp around the actuator component 328 and clamp leaflets against the actuator component, similar to the embodiments described above.

FIG. 20A illustrates another embodiment of a commissure support element 400 comprising a unitary or wire-form body 402. The commissure support element 400 can comprise an annular or curved coupling portion or collar portion 404 at least partially enclosing a first area or coupling region 406. The commissure support element 400 can further comprise first and second members 408 and 410 extending from the collar portion 404 at an angle to the plane of the collar portion (e.g., 90°). More particularly, the first member 408 can comprise a first end portion 412 coupled to the collar portion 404 and a distal end portion 414. The second member 410 can comprise a first end portion 416 coupled to the collar portion opposite the first end portion 412 of the first member, and a second end portion 418. The second end portions 414 and 418 of the first and second members can be coupled together by a member 420 extending therebetween. The member 420 can be straight or curved. Members or portions 434 and 436 (FIG. 23) can space or offset the first and second members 408 and 410 away from the collar portion 404 (e.g., radially inwardly relative to the frame of which the actuator component is a part), as best shown in FIGS. 22 and 23.

Referring again to FIG. 20A, the first and second members 408 and 410 can define a U-shaped, longitudinally-extending leaflet-receiving space or window 422 between them that extends between the collar portion 404 and the member 420. The wire-form body 402 can have a rectangular cross-section, as shown in FIG. 20A, or may be round or cylindrical, as shown in FIG. 20B. The member 420 connecting the first and second members 408 and 410 can also be curved, as in FIG. 20B.

In certain embodiments, the commissure support element 400 can be configured for attachment to a post, such as an actuator component of a mechanically-expandable prosthetic heart valve configured according to any of the embodiments described herein. FIG. 21 illustrates a representative example of an actuator component 424, which may be configured according to any of the actuator components described herein, and further configured to receive the commissure support element 400. The actuator component 424 can define a groove, slot, or recess 426 at the outflow end 428 of the component on a radially outward surface 430 of the component. The cross-section of the actuator component 424 (or of the outer housing thereof) can have a shape or aspect ratio corresponding to the shape of the coupling region 406 (e.g., rectangular or square, with or without rounded corners, or curved or cylindrical, etc.).

Figure 23:
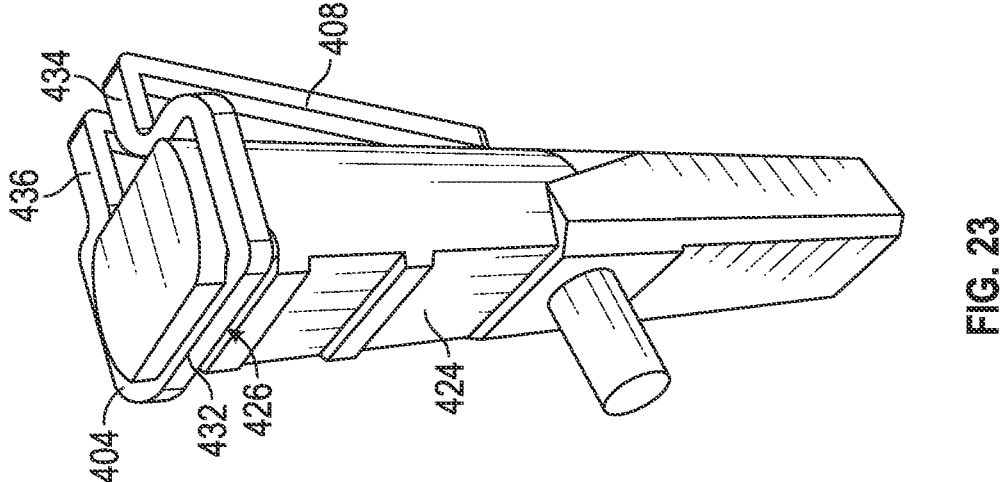
FIGS. 22 and 23 are perspective views illustrating placement of the commissure support element of FIG. 20A on the actuator component of FIG. 21.
Figure 22:
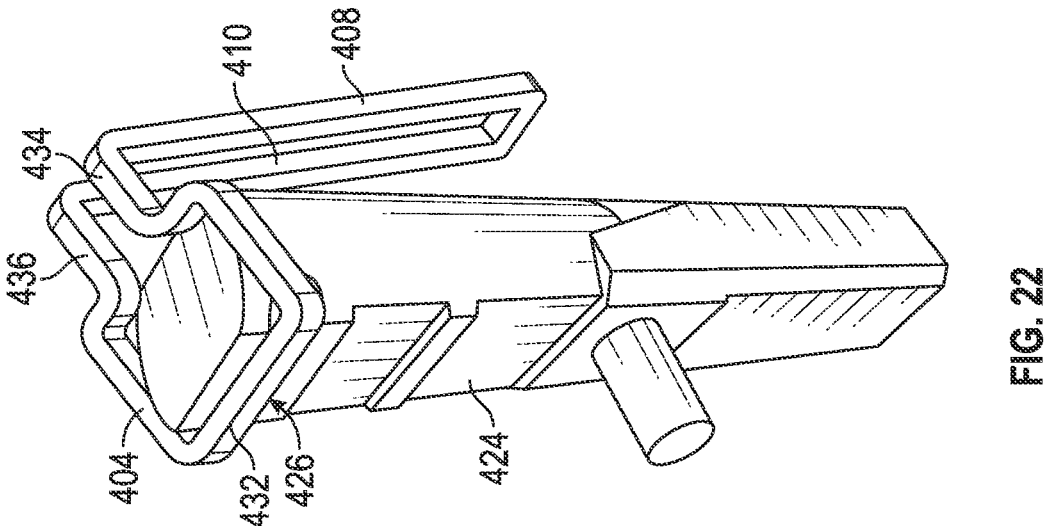

FIGS. 22 and 23 illustrate placement of the commissure support element 400 on the actuator component 424. Referring to FIG. 22, a radially outward (relative to the frame of which the actuator component is a part) portion or member 432 of the collar portion 404 can be located or situated in the recess 426. The element 400 can then be rotated such that the remaining portions of the collar portion 404 are brought into engagement with the actuator component 424 with the first and second members 408, 410 disposed radially inwardly of the actuator element on the inside of the prosthetic valve. In certain embodiments, the recess 426 can help to retain the commissure support element in place on the actuator component. In certain embodiments, the collar portion 404 and the actuator component 424 can be configured such that the collar portion snaps into place or is held in the use position to aid in retaining the commissure support element on the actuator component. When the commissure support element 400 is coupled to the actuator component 424, the first and second members 408, 410 can extend in a direction along the longitudinal axis of a prosthetic heart valve of which the actuator component is a part in a direction toward the inflow end of the valve.

In certain embodiments, the commissure support element 400 can be formed or bent from a wire member, and/or can be cut (e.g., laser cut) from a plate or sheet. The commissure support element 400 can comprise a single or multiple layers of the same or different materials (e.g., metals, polymers, etc.), as described above.

Figure 24B:
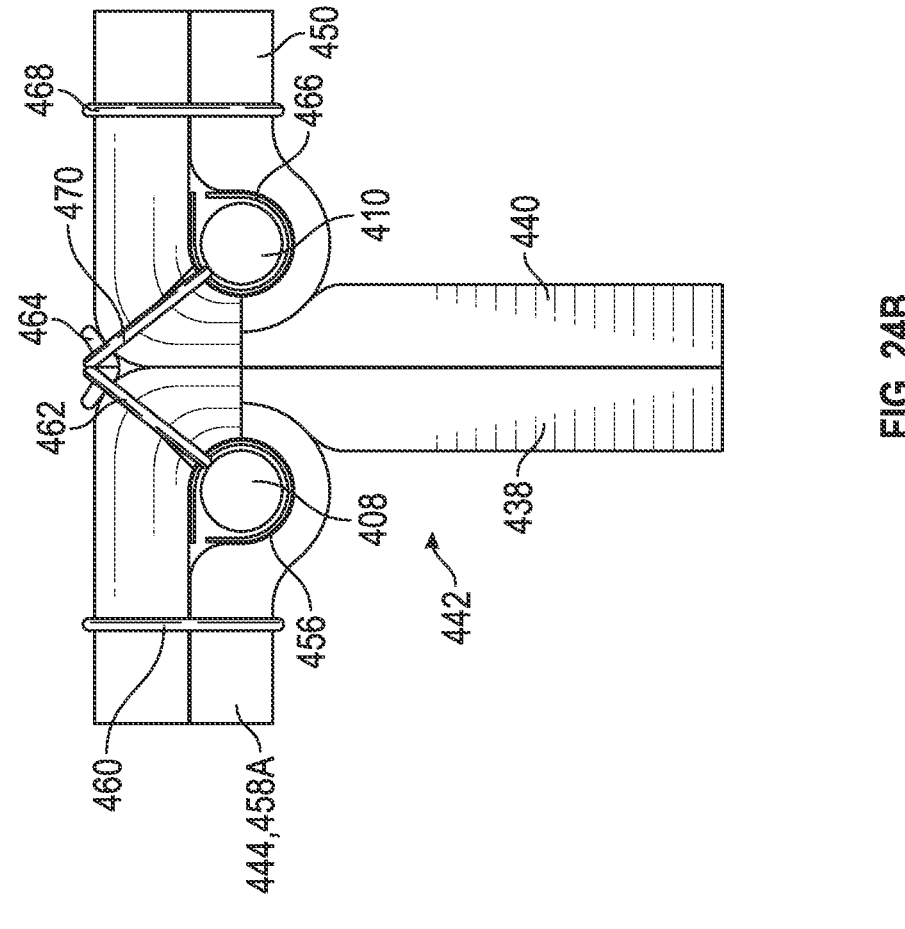
FIGS. 24A-24D and 25 are various views of a commissure formed with the commissure support element of FIG. 20A on the actuator component of FIG. 21, according to one embodiment.
Figure 24A:
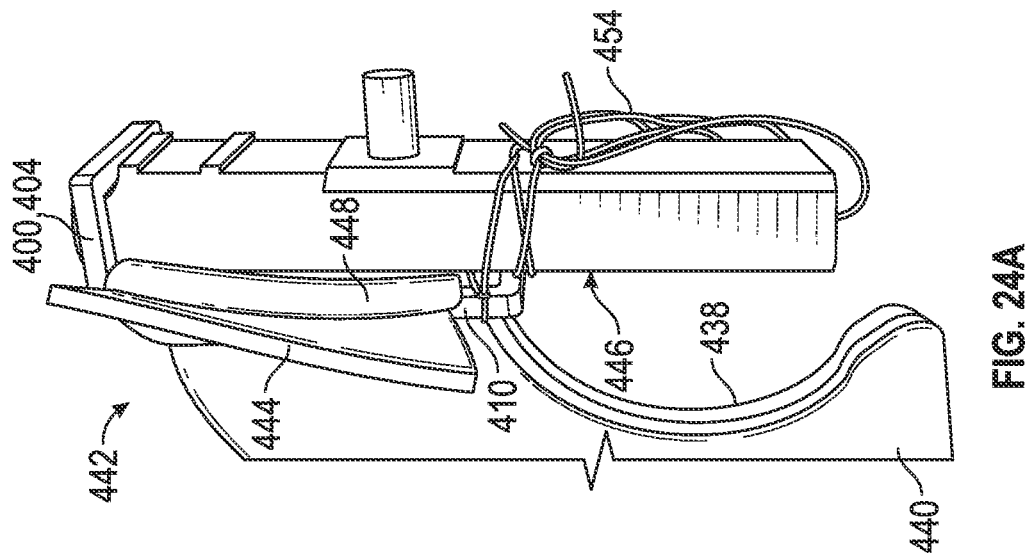
Figure 24D:
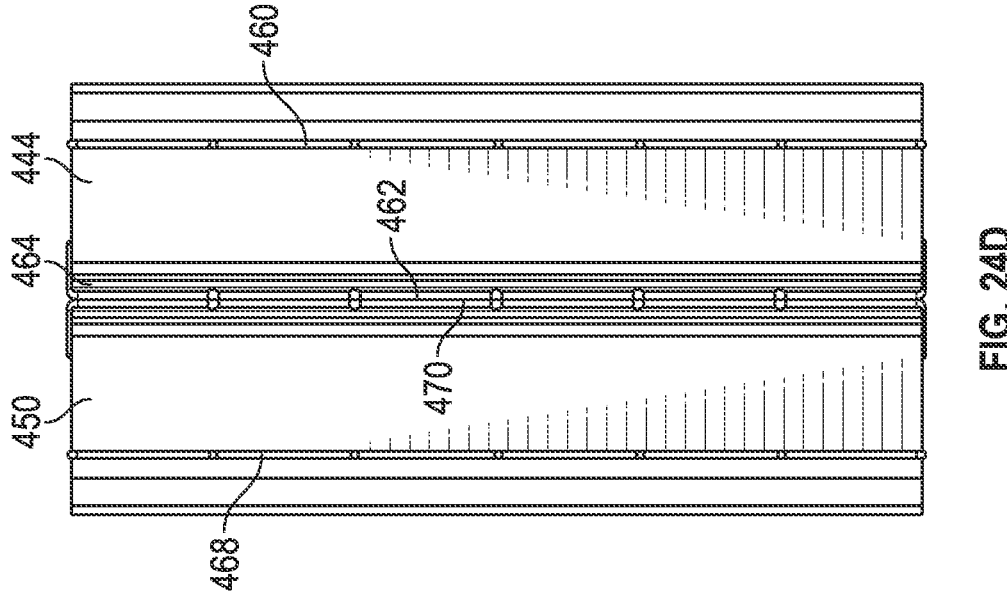
Figure 24C:
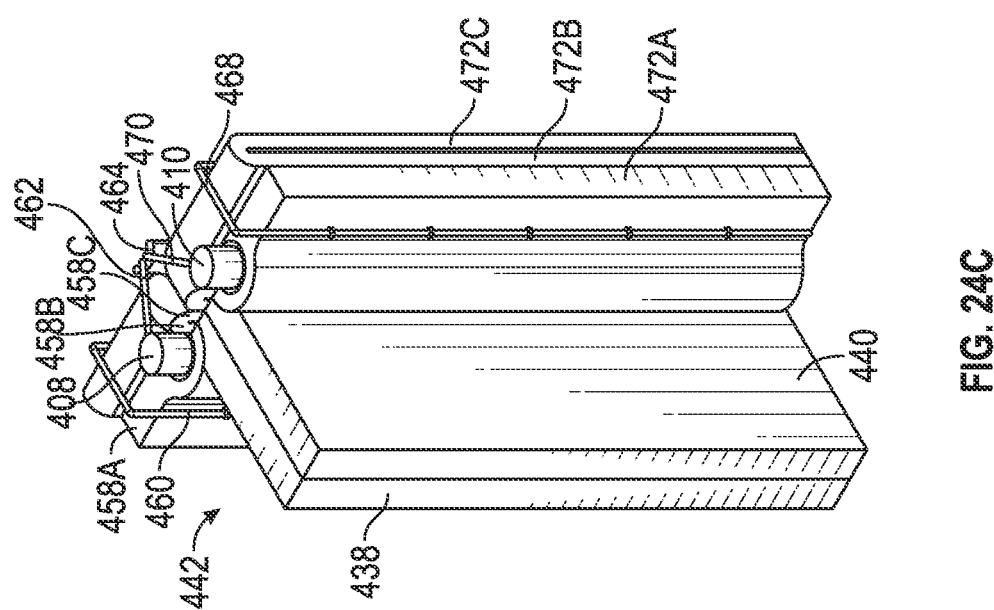
Figure 25:
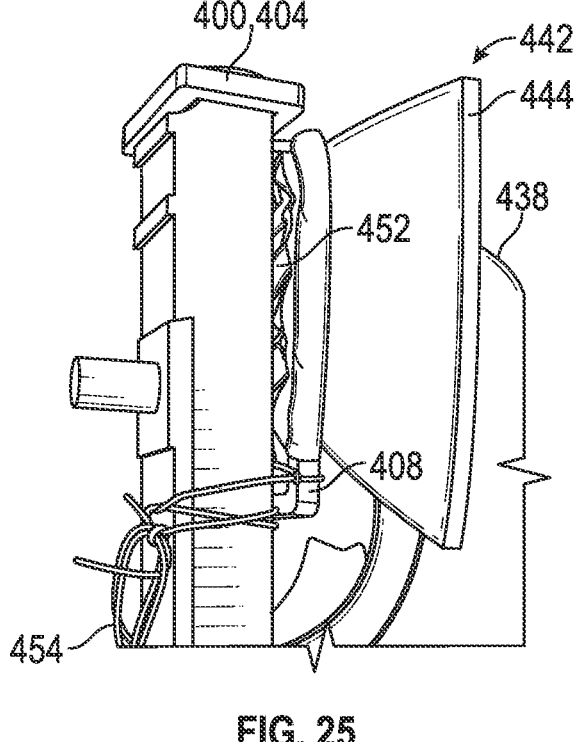

FIGS. 24A-24D and 25 illustrate two leaflets 438 and 440 disposed in the commissure support element 400 to form a commissure 442. Each of the leaflets can comprise at least one leaflet tab or commissure tab on each side, which can be inserted through the leaflet-receiving window 422 (FIG. 20A) of the commissure support element and secured to the commissure support element, to the actuator component 424, and/or to the commissure tab of the adjacent leaflet. For example, referring to FIG. 24B, the leaflet 440 can comprise a commissure tab 450 (e.g., a lower tab and/or an upper tab) inserted through the leaflet-receiving window 422 (FIG. 20A), and folded around the second member 410. A portion of the commissure tab 450 can contact or lie against the radially-inward surface 446 of the actuator element. A portion of the commissure tab 450 can be folded to form a fold or cuff 448. Referring to FIG. 25, a leaflet tab 444 (e.g., a lower tab and/or an upper tab) of the leaflet 438 can be inserted through the leaflet-receiving window 422 and folded around the first member 408 to form a cuff in a similar manner. In certain embodiments, the leaflet tabs can space the second end portions 414 and 418 (FIG. 20A) of the first and second members 408, 410 away from the actuator component 424.

In certain embodiments, the leaflet tabs 444 and 450 can be attached together in the space between the leaflet-receiving window 422 and the actuator component 424, such as by sutures 452 (FIG. 25). The leaflets can further be attached to the first and second members 408, 410 (e.g., to the second end portions of the members) by sutures 454, although in other embodiments the sutures 454 may be omitted.

FIG. 24B illustrates a top plan view of the commissure assembly 442. The leaflet tab and/or tabs 444 of the leaflet 438 can be wrapped or folded around the axial member 408 such that there are three layers 458A, 458B, and 458C (FIG. 24C). The tab 450 of the leaflet 440 can be wrapped or can extend around the axial member 410. In certain embodiments, upper tabs of the leaflets can be folded downwardly at a location radially outward of the members 408 and 410. A stitch protector member 456 can be disposed around the axial member 408 between the axial member and the layers of the leaflet tab 444. A first attachment line, stitch, line, or suture line 460 can secure the layers 458A, 458B, and 458C together at a location circumferentially offset from the axial member 408 (to the left in FIG. 24B). A second suture line 462 can extend through the stitch protector member, through at least the leaflet tab layers 458B and 458C, and through a wedge member 464 disposed radially outwardly of the commissure support element 400. The wedge member 464 can be disposed between the leaflet tabs 444 and 450 against their respective radially outward surfaces. The leaflet tab 450 can be folded similarly, with a stitch protector layer 466 disposed around the axial member 410, a suture line 468 extending through the layers 472A, 472B, and 472C of the folded leaflet tab circumferentially offset from the axial member 410, and a suture line 470 extending through the suture protection member 466, the leaflet tab 450, and the wedge member 464. FIGS. 24C and 24D provide a perspective view and a rear elevation view (e.g., looking radially inwardly) of the commissure 442.

In certain embodiments, the commissure support element 400 can provide certain advantages, such as ease of manufacturing, ease of attachment to the actuator component, and/or ease of assembly of the commissure.

Figure 26:
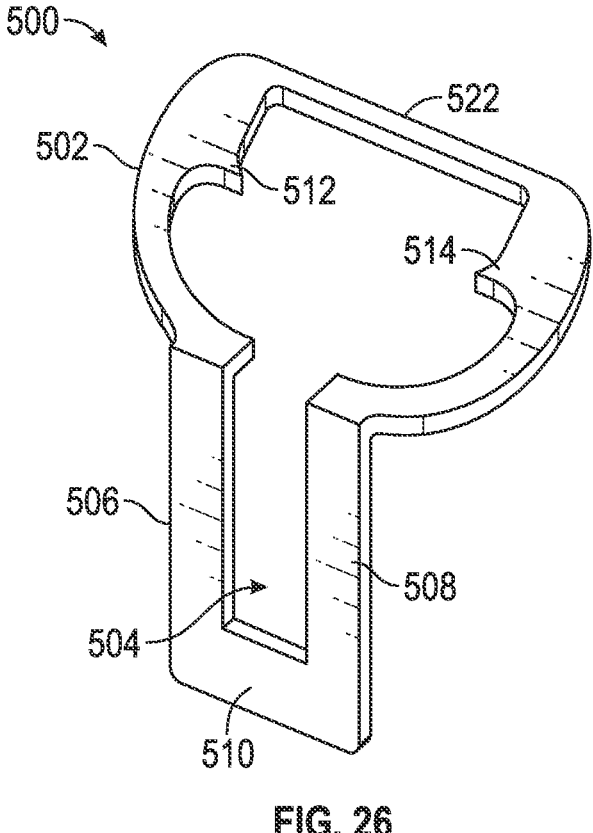
FIG. 26 is a perspective view of another embodiment of a commissure support element including projections on the inner perimeter of the collar portion.

FIG. 26 illustrates another embodiment of a commissure support element 500 comprising a unitary or wire-form body similar to the element 400 of FIG. 20A. The commissure support element can include a curved coupling portion or collar portion 502, and a leaflet-receiving window 504 defined by first and second members 506 and 508 extending downwardly (e.g., toward the inflow end of a prosthetic valve) from the collar portion 502, and a cross member 510 extending between the first and second members at the opposite end of the window 504 from the collar portion 502.

Figure 27:
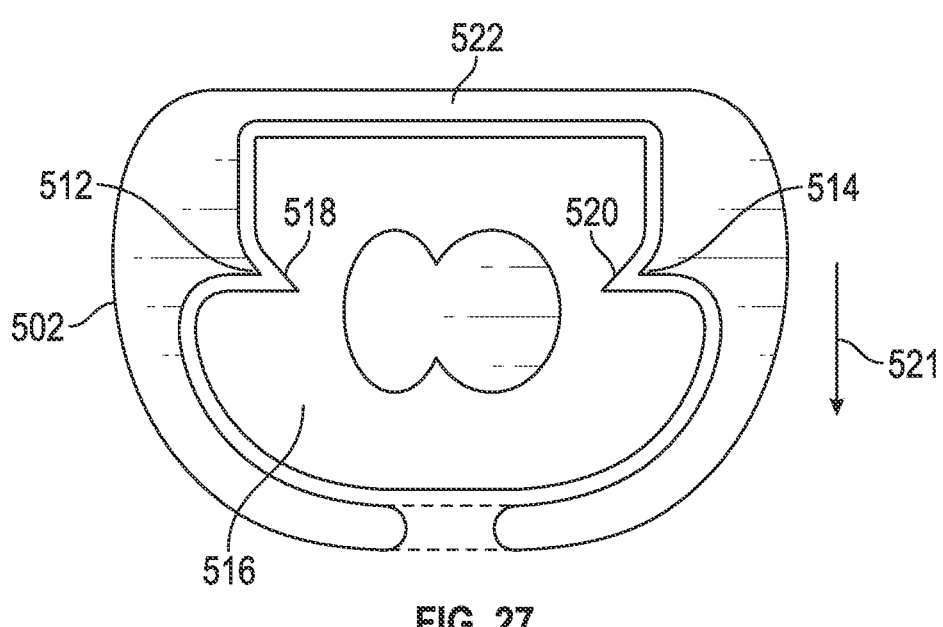
FIG. 27 is a top plan view of the commissure support element of FIG. 26 coupled to an actuator component.

The inner perimeter of the collar portion 502 can comprise a first inwardly-extending projection or protrusion 512 and a second inwardly-extending projection or protrusion 514 on the opposite side of the collar from the first projection and oriented generally toward the first projection. Referring to FIG. 27, the collar portion 502 of the commissure attachment element 500 can be configured for attachment to a post or actuator component 516 of a mechanically-expandable prosthetic heart valve adapted to receive the collar portion. For example, the actuator component 516 can comprise a notch, slot, or recess 518 shaped to correspond to the projection 512 and a notch, slot, or recess 520 shaped to correspond to the projection 514. The projections 512 and 514 can be configured to contact the radially inward surfaces of the recesses 518 and 520, such as during diastole. During diastole, the leaflets of the commissure can tend to pull the commissure support element radially inwardly in the direction of arrow 521. Thus, the projections 512 and 514 can contact the walls of the recesses 518 and 520 of the actuator component to brace the support element and prevent significant motion of the support element. This interaction can also relieve a substantial proportion of the stress or force applied to the rear (e.g., radially outward) member 522 of the collar portion 502, allowing the rear member 522 to be made thinner. This, in turn, can decrease the crimped diameter or profile of the prosthetic heart valve. The side portions of the collar member from which the projections extend can also be thicker to accommodate the forces.

In FIG. 26, the first and second members 506 and 508 are coupled together at their inflow ends by the cross member 510. However, in certain embodiments the cross member 510 can be omitted, as in the embodiment of FIG. 27.

Figure 28:
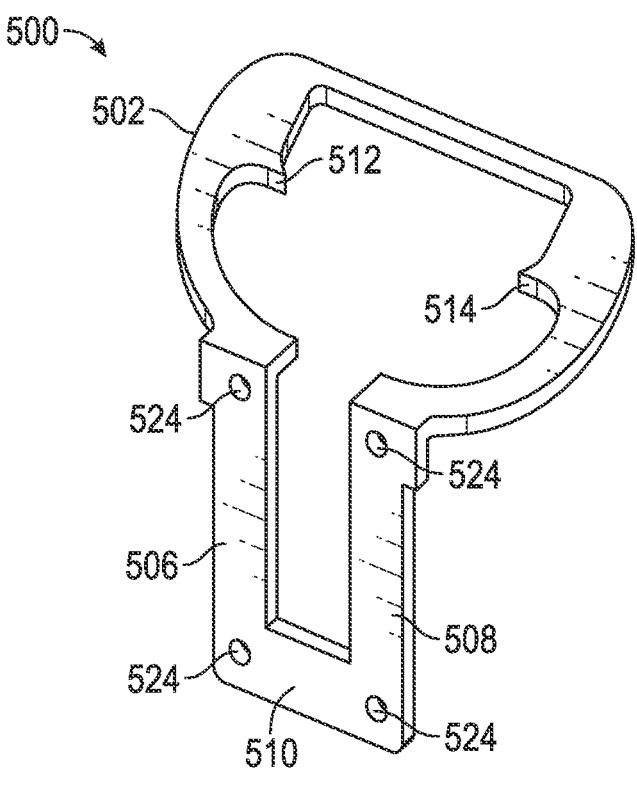
FIGS. 28 and 29 are perspective views of additional embodiments of the commissure support element of FIG. 26.

FIG. 28 illustrates another configuration of the commissure support element 500 in which the first and second members 506 and 508 and/or the cross member 510 include a plurality of openings 524 (e.g., at the inflow and outflow ends of the members 506 and 508). Suture(s) can be inserted or threaded through the openings to attach the commissure support element to an actuator component, and/or to attach leaflets to the commissure support element. For example, in certain embodiments sutures can be threaded or looped between the upper openings 524 such that the sutures extend above the leaflet tabs to retain the leaflets in position, and/or to draw the upper portions of the members 506 and 508 toward one another to apply pressure to the leaflet tabs.

Figure 29:
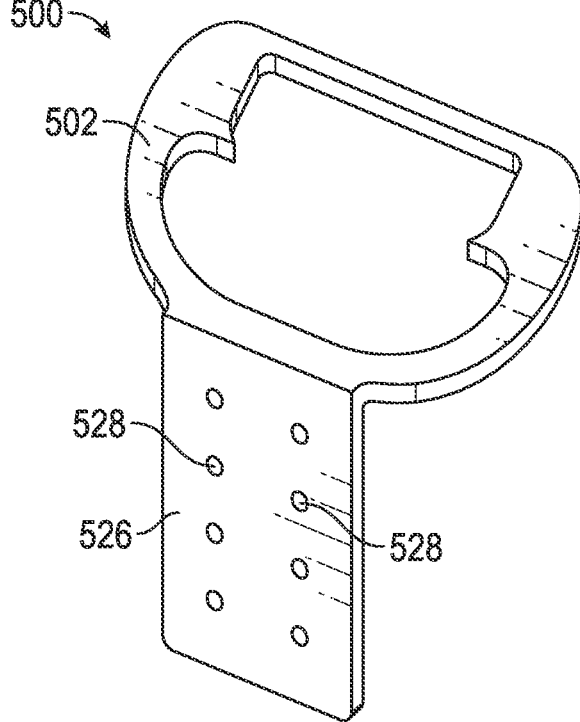

FIG. 29 illustrates another embodiment of the commissure support element 500 in which the support element comprises a planar member or plate member 526 extending from the collar portion 502 perpendicular, or substantially perpendicular, to the collar portion. The plate member 526 can comprise a plurality of openings 528. In the illustrated embodiment, the openings 528 are arranged in two vertical columns of four openings, although in other embodiments the plate member 526 can have any number of openings arranged in any arrangement including a single opening or no openings. The leaflet tabs of a commissure can be wrapped around the plate member 526. In certain embodiments, the leaflet tabs can be secured with sutures through the openings 528. In certain embodiments, sutures can be inserted through the openings 528 to attach the commissure support member and/or the commissure to an actuator component. In other embodiments, the first and second members of FIG. 28 can comprise openings arranged in columns similar to FIG. 29.

Figure 30:
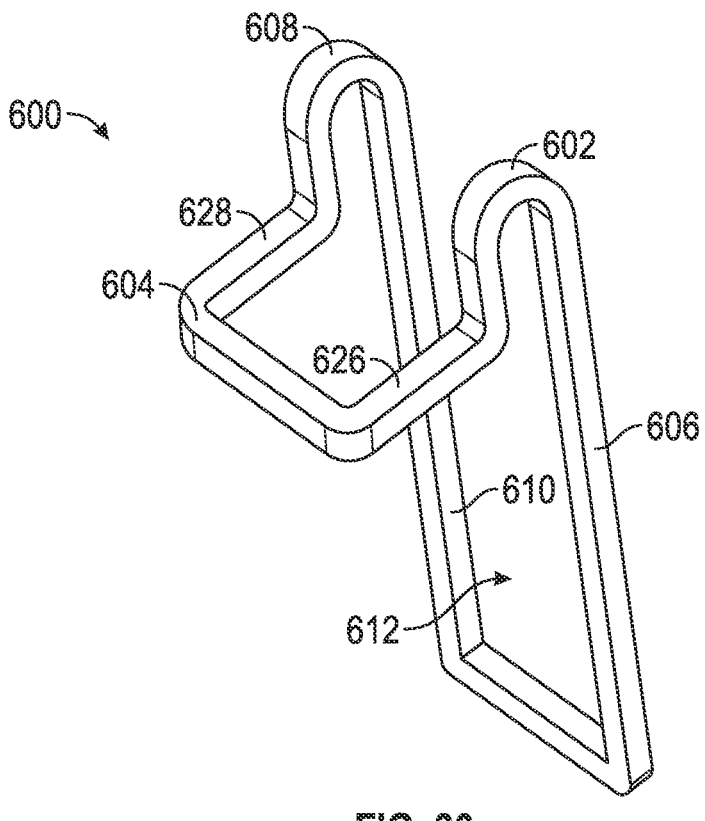
FIG. 30 is a perspective view of a commissure support element according to another embodiment.

FIG. 30 illustrates another embodiment of a commissure support element 600 configured similarly to the support element 400 of FIG. 20A. The commissure support element 600 comprises U-shaped curved member 602 extending between the collar portion 604 and the first axial member 606. The support element further comprises a similar curved member 608 extending between the collar portion 604 and the second axial member 610. The curved members 602 and 608 can curve upwardly (e.g., in the outflow direction) from the collar portion 604, which can lengthen the first and second members 606 and 610 of the leaflet-receiving window 612. The apices of the curved members 602 and 608 can have any height. The members 602 and 608 can also space the first and second members 606 and 610 any specified distance from the collar portion 604 (e.g., radially inwardly when coupled to a frame). In certain embodiments, the commissure support element 600 can be made from a wire-form member, and/or can be laser cut from a sheet of material and bent, curved, or folded into the specified shape, as described above.

Figure 31:
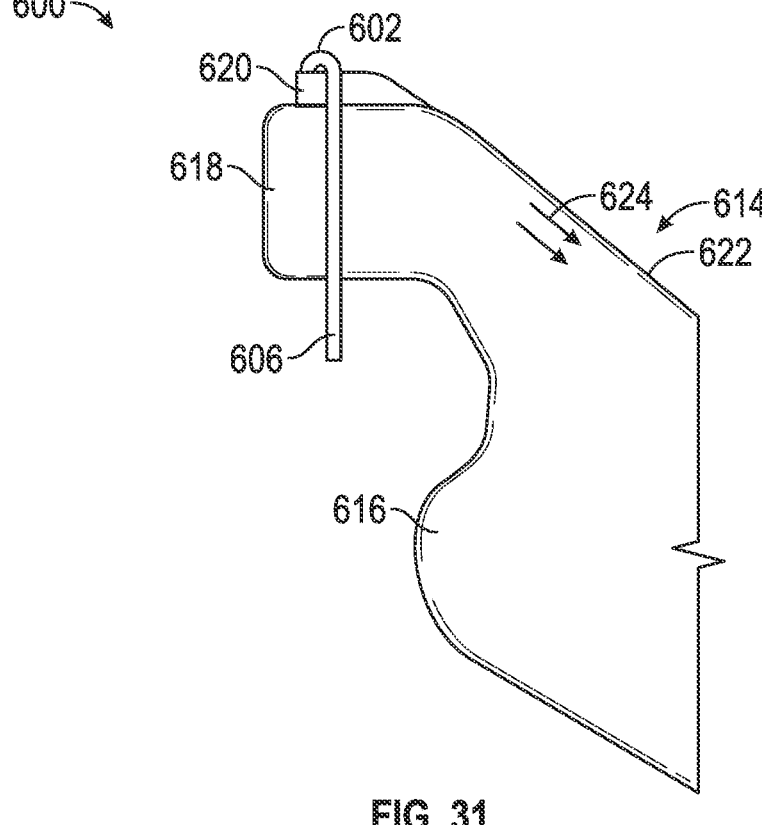
FIG. 31 is a side elevation view of a commissure formed with the commissure support element of FIG. 30.

As noted above, the curved members 602 and 608 can lengthen the first and second members 606 and 610. This, in turn, can lengthen the leaflet-receiving window 612. In certain embodiments, the longer leaflet-receiving window can reduce stress on the leaflets and the corresponding risk of tearing during valve operation. For example, FIG. 31 illustrates a side elevation view of a commissure 614 including leaflets 616 received in the commissure support element 600. The actuator component and frame of the prosthetic valve are omitted for clarity.

The longer leaflet-receiving window 612 (FIG. 30) can allow the window to accommodate leaflet tabs 618 which include additional tabs 620 disposed along the outflow edge 622 of the leaflets 616. In the illustrated configuration, the outflow edge 622 can slope downwardly in the direction of the inflow end of the valve. During diastole, the leaflets 616 can tend to extend radially inwardly to coapt with each other, which can exert corresponding stresses, represented schematically by arrows 624, on the leaflets at the location of attachment to the commissure support element 600. This can also result in the application of force to the commissure support element. The angled outflow edge 622 of the leaflets can result in a non-uniform stress distribution along the attachment of the leaflets to the leaflet-receiving window 612. The additional leaflet tabs 620, and/or lengthened leaflet tabs 618, together with the longer leaflet-receiving window 612, can result in a more even stress distribution along the leaflet tabs at the location(s) of attachment to the commissure support element. Including the additional leaflet tabs 620 can also result in the development of maximum stresses within the bodies of the leaflets, rather than at the outflow edges, reducing the risk of tearing.

Although the configuration illustrated in FIG. 30 shows the curved members 602 and 608 extending directly from side members 626 and 628 of the collar portion 604 resulting in a spacing equal to or substantially equal to the length of the major axis of the collar portion 604, the curved members may also be positioned closer together. For example, the collar portion 602 can be configured similarly to the collar portion 404 of FIG. 20A, and the curved members can extend from the location of attachment of the members 408 and 410. Such a configuration can be configured to lock or snap into place on the actuator component, as described above. Curved members such as the members 602 and 608 can be incorporated into any of the commissure support element embodiments described herein.

Figure 32:
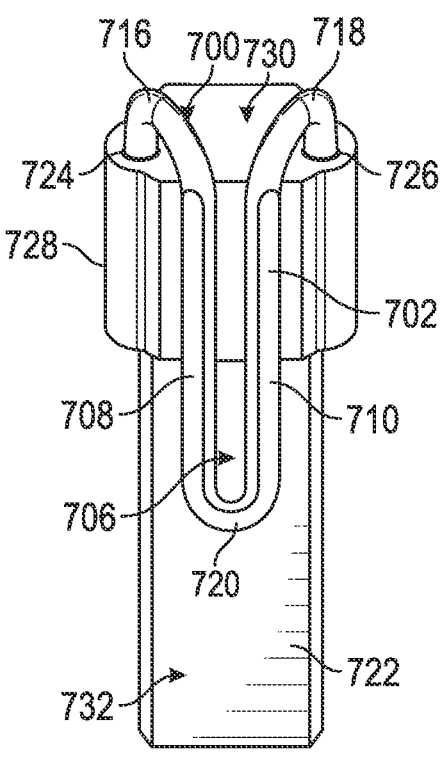
FIG. 32 is a perspective view of another embodiment of a commissure support element coupled to a corresponding actuator component.
Figure 33:
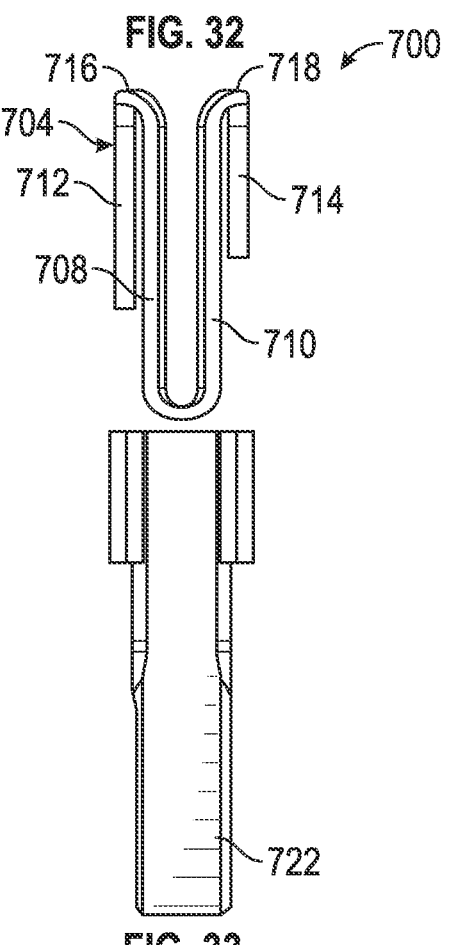
FIG. 33 is a side elevation view of the commissure support element and the actuator component of FIG. 32 illustrating the coupling portion of the commissure support element.

FIGS. 32 and 33 illustrate another embodiment of a commissure support element 700 configured as a unitary wire-form body 702 including a coupling portion 704 (FIG. 33) and a leaflet-receiving window 706 (FIG. 32) defined by axially-extending first and second members 708 and 710. Referring to FIG. 33, the coupling portion 704 can comprise a pair of coupling members 712 and 714. The coupling member 712 can be coupled to the first axial member 708 by a curved portion or member 716, and the coupling member 714 can be coupled to the second axial member 710 by a curved portion or member 718. In certain embodiments, the coupling portions 712 and 714 can curve by 180° such that the first and second axial members 708 and 710 extend parallel or substantially parallel to the coupling members 712 and 714, for example toward the inflow end of a prosthetic heart valve of which the actuator 722 is a part, although other configurations are possible. In the illustrated embodiment, the angular or circumferential spacing between the coupling members 712 and 714 can be greater than the angular spacing between the first and second axial members 708 and 710, although in other embodiments the angular spacing may be the same or less than the spacing between the members 708 and 710. Accordingly, the curved members 716 and 718 can be angled toward one another.

The first and second axial members 708 and 710 can be coupled together at their inflow end portions by a member 720 (FIG. 32). The member 720 can be curved or straight. The members 708, 710, and 720 can at least partially define the leaflet-receiving window 706, which can be open at the top. Referring to FIG. 33, in certain embodiments one of the coupling members 712 or 714 may be longer than the other. For example, in the embodiment shown in FIG. 33 the coupling member 712 is longer than the coupling member 714, although the opposite configuration can also be implemented. The coupling members 712 and 714 may also have equal lengths, such as in FIG. 34.

Referring again to FIG. 32, the commissure support element 700 can be received by or coupled to a post or actuator component 722 of a mechanically-expandable prosthetic heart valve, which can be configured similarly to any of the actuator components described herein. The actuator component 722 can comprise a pair of tubular openings or channels 724 and 726 configured to receive the coupling members 712 and 714, respectively. In the illustrated embodiment, the channels 724 and 726 can be located on the sides of the actuator component at the outflow end portion 728 of the actuator component, although the channels may be located anywhere around the perimeter of the actuator component and at any location along its length. The commissure support element 700 can be configured such that when coupled to the actuator component 722, the curved members 716 and 718 extend above (e.g., in the outflow direction) an upper surface 730 of the actuator component, although the support element may also be disposed elsewhere along the length of the actuator component between the inflow and outflow end portions of the actuator component.

In certain embodiments, the axial length of the leaflet-receiving window 706 can correspond to the length of the leaflet tabs of the leaflets of the commissure in order to restrain axial movement of the leaflet tabs. The length of the curved members 716 and 718 can be configured such that the first and second axial members 708 and 710 are offset radially inwardly from an interior or radially inward surface 732 of the actuator component. The distance between the axial members 708 and 710 and the surface 732 of the actuator component can be selected to allow the leaflet tabs to extend between the members 708, 710 and the surface 732, and to enable clamping of the leaflet tabs by the members 708, 710 against the surface 732. The spacing between the members 708 and 710 can also be selected to press the leaflets together to retain the commissure in place.

The commissure support element 700 can be formed from a wire-form body as described above, or can be laser cut from a plate or sheet and bent, folded, and/or formed into the specified shape. The commissure support element 700 can comprise a metal material, a polymeric material, and/or combinations or layers thereof.

Figures 34, 35:
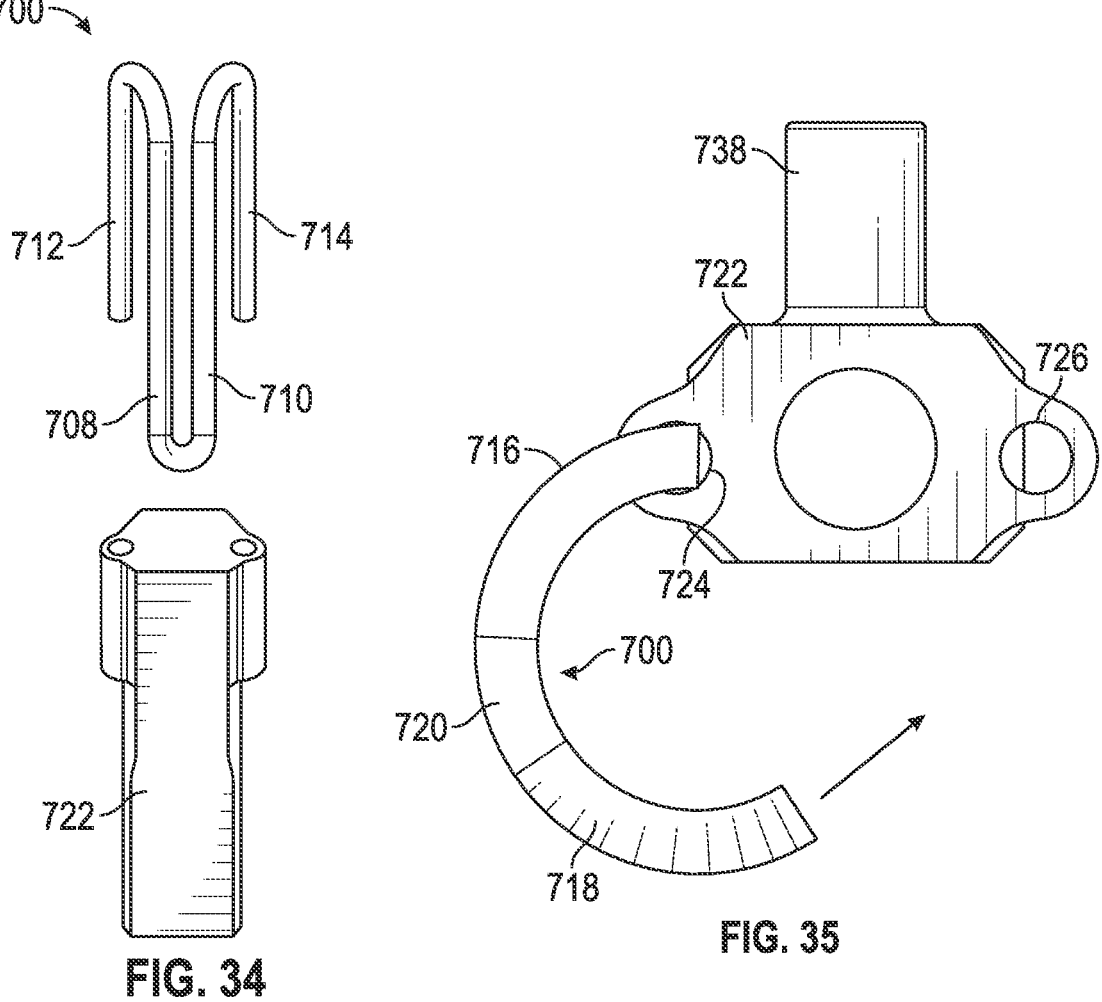
FIG. 34 is a side elevation view of the commissure support element and the actuator component of FIG. 32, according to another embodiment.
FIGS. 35 and 36 are top plan views illustrating connection of the commissure support element of FIG. 32 to the actuator component.
Figure 36:
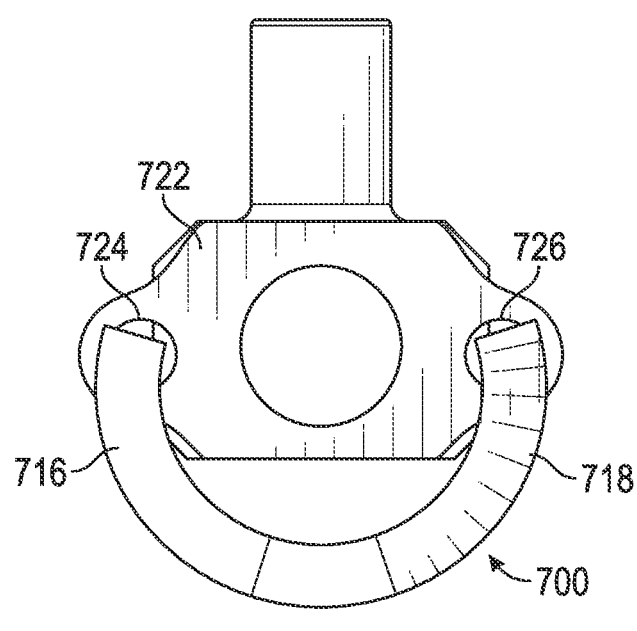

FIGS. 35 and 36 illustrate the steps of coupling the commissure support member 700 to the actuator component 722, according to one embodiment. In FIG. 35 the coupling member 712 (FIG. 33) can be inserted into the corresponding channel 724 with the commissure support element rotated such that the coupling member 714 is disposed radially inwardly of the actuator component 722. In embodiments where the coupling member 712 is longer than the coupling member 714, the coupling member 712 may be inserted into the actuator component first. With the coupling member 712 at least partially advanced into the channel 724, the commissure support element can be rotated about the coupling member 712 to align the coupling member 714 with the channel 726. The commissure support element can then be advanced in the direction of the inflow end of the prosthetic valve such that the coupling members 712 and 714 are inserted into the corresponding channels 724 and 726 by a specified distance. In certain embodiments, inserting the coupling members into the actuator component one at a time can simplify the assembly process, although the coupling members may also be advanced into the openings at the same time.

Figure 37:
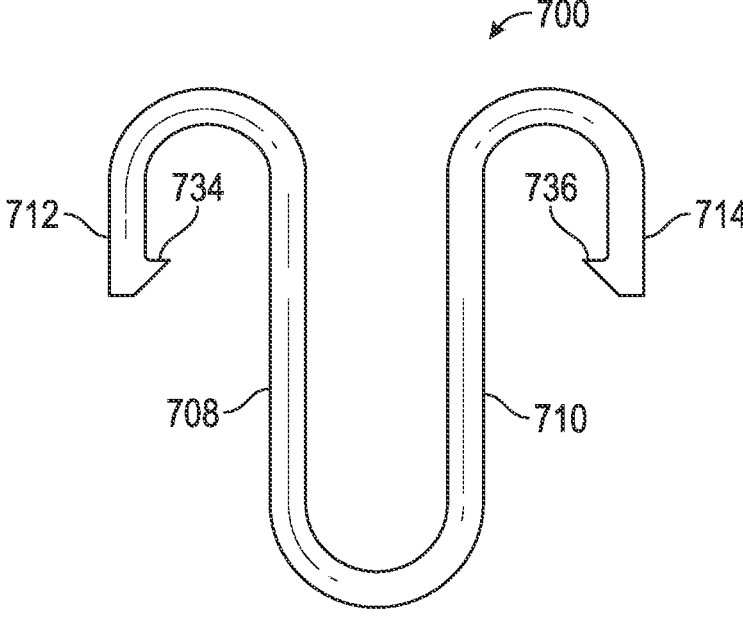
FIG. 37 is a front elevation view of another embodiment of a commissure support element.

FIG. 37 illustrates another embodiment of a commissure support element 700 in which the coupling members 712 and 714 comprise tabs, projections, or protrusions 734, 736 at their distal end portions. The protrusions 734 and 736 can be configured to engage corresponding recesses of the actuator component 722 in order to retain the commissure support element in place on the actuator component.

In other embodiments, the first and second axial members 708 and 710 can be angled toward each other such that the leaflet-receiving window 706 is V-shaped. In yet other embodiments, the first and second axial members 708 and 710 can overlap at any location along their lengths (e.g., to form an "X" or cross). In such embodiments, the first and second axial members 708 and 710 can be pulled apart or opened in order to receive the leaflets of a commissure, and can return to the overlapped configuration to press the leaflets together.

Figure 38:
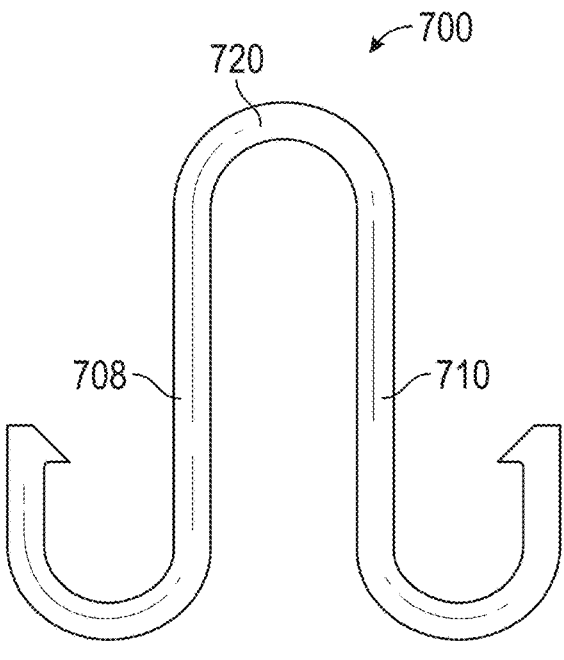
FIG. 38 is a front elevation view of another embodiment of a commissure support element in which the first and second members extend upwardly from the coupling portion.
Figure 39:
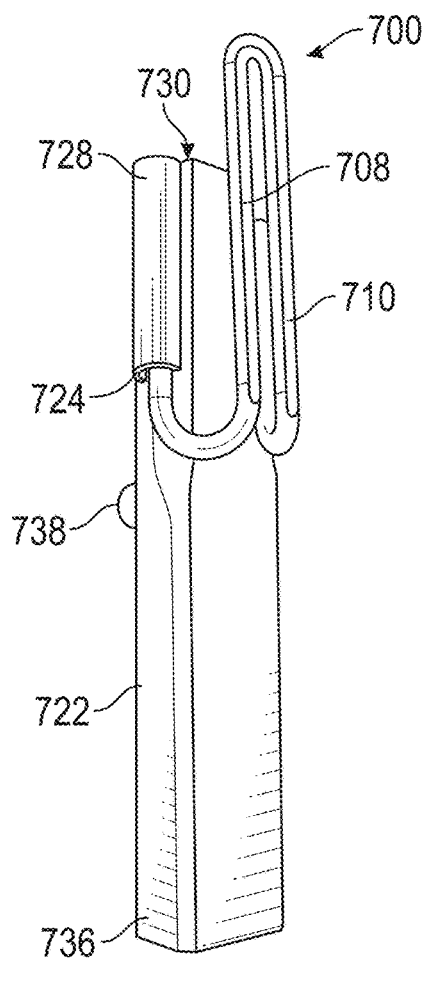
FIG. 39 is a perspective view of the commissure support element of FIG. 38 coupled to an actuator element.

In certain embodiments, the commissure support elements described herein can be coupled to the actuator components such that the first and second axial members extend from the coupling portion upwardly in the direction of the inflow end of the prosthetic valve. For example, FIG. 38 illustrates another embodiment of the commissure support element 700 configured for attachment to an actuator element with the member 720 located at the outflow end of the element, and FIG. 39 shows the element 700 coupled to a modified embodiment of the actuator component 722. More particularly, the channels 724 and 726 can be located between the inflow end 736 and the outflow end 728 of the actuator component, such as offset from the outflow surface 730 in a direction toward the hinge pin member 738, or located between the pin member 738 and the surface 730. When the commissure support element is inserted into the channels 724 and 726, the curved members 716 and 718 can curve upwardly such that the first and second axial members 708 and 710 extend in the direction of the outflow end of the prosthetic valve.

Referring to FIGS. 40 and 41, in certain embodiments the angle of the first and second members 708 and 710 relative to the actuator component 722 can be varied. For example, referring to FIG. 40, the first and second members 708 and 710 can be parallel, or substantially parallel, to the longitudinal axis of the actuator component 722. Referring to FIG. 41, in certain embodiments the first and second members 708 and 710 can be flexible, and can be angled away from the actuator component 722 and radially inwardly toward the central axis of the prosthetic valve (FIG. 1). In certain embodiments, where the first and second axial members 708 and 710 are unrestrained at the outflow end of the actuator component, the angle of the axial members can change during valve operation, for example by flexing about the curved members 716 and 718. This can allow a more even stress distribution along the attachment between the leaflets 746 and the commissure support element 700 during valve operation, and particularly during diastole, as indicated schematically in FIGS. 40 and 41.

FIG. 42 illustrates another embodiment in which a commissure member or plate 740 is coupled to the actuator component 722. The commissure plate 740 can comprise a portion or flange 742 comprising a plurality of openings 744. In certain embodiments, the commissure plate 740 can comprise a similarly configured flange on both sides of the actuator element, or on only one side. In certain embodiments the commissure plate 740 can be sutured to the actuator component 722 by sutures extending through the openings 744. In certain embodiments, the commissure plate 740 can include the channels 724 and 726 for receiving the coupling members of the commissure support element. In certain embodiments, the commissure plate 740 can be integrally formed with the commissure support element 700, or with the actuator component 722. The leaflets of the commissure can also be sutured to the commissure plate 740 through the openings 744.

Figure 43:
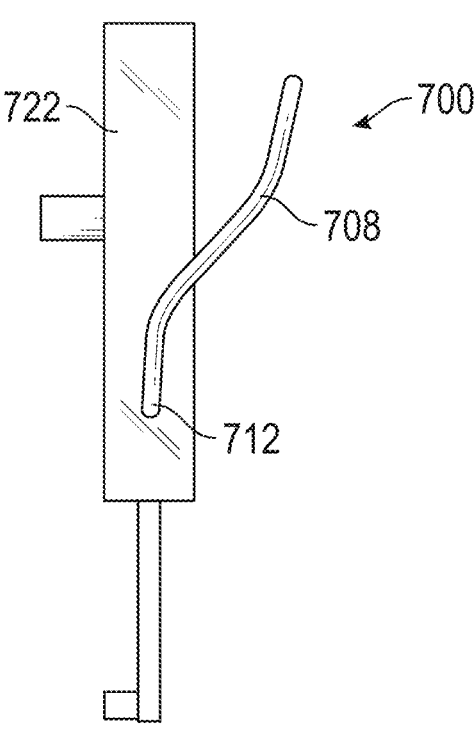
FIGS. 43 and 44 illustrate another embodiment of a curved commissure support element in which the coupling members are attached to an actuator component and the first and second members extend in a direction toward the outflow end of the prosthetic valve.
Figure 44:
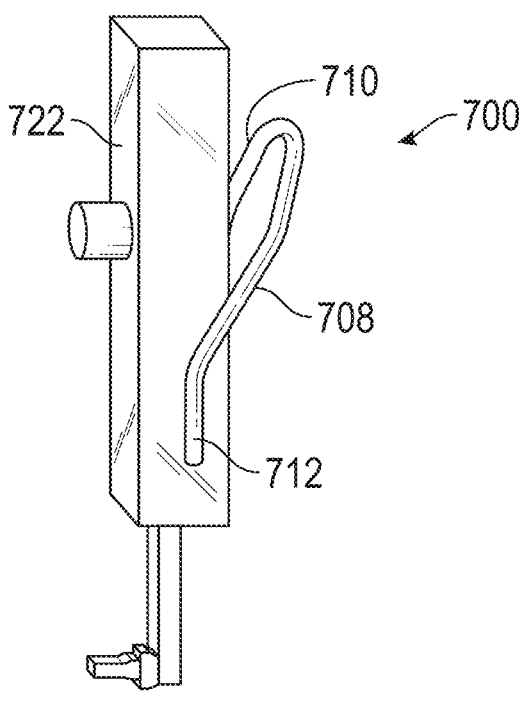

FIGS. 43 and 44 illustrate another embodiment of the commissure support element 700 in which the coupling members 712 and 714 are attached to or received in the actuator component 722 and extend in a direction toward the inflow end of the prosthetic valve, while the first and second members 708 and 710 extend generally in the direction of the outflow end. The first and second axial members 708 and 710 can comprise one or more curved portions such that the members extend radially inwardly away from the actuator component and upwardly in the outflow direction.

Figure 45:
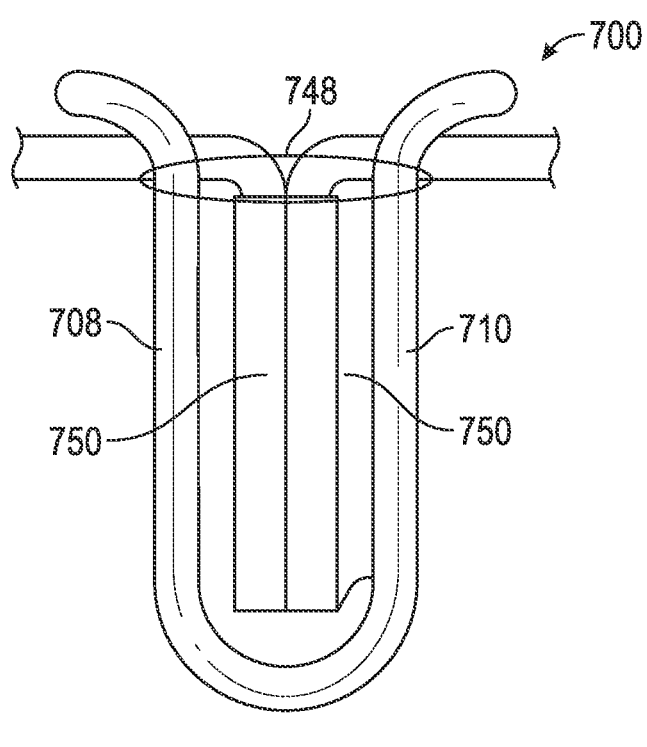
FIG. 45 is a front elevation view of a commissure support element with the first and second members tied together with sutures, according to another embodiment.
Figure 47:
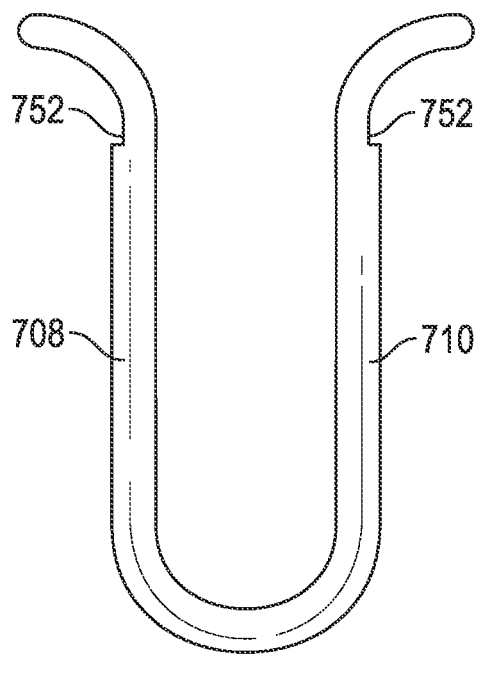
FIG. 47 is a front elevation view of a commissure support element including notches for retaining sutures, according to another embodiment.

The commissure support elements described herein can also include any of a variety of features configured to enable the commissure support elements to engage the leaflets of the commissure. For example, FIG. 45 illustrates a commissure support element 700 comprising suture 748 wrapped around the outflow ends of the first and second axial members 708, 710 above the leaflets 750 to press the members against the leaflets 750. FIG. 47 illustrates another configuration of the commissure support element comprising notches 752 in the axial members 708 and 710 to retain the sutures 748.

Figure 46:
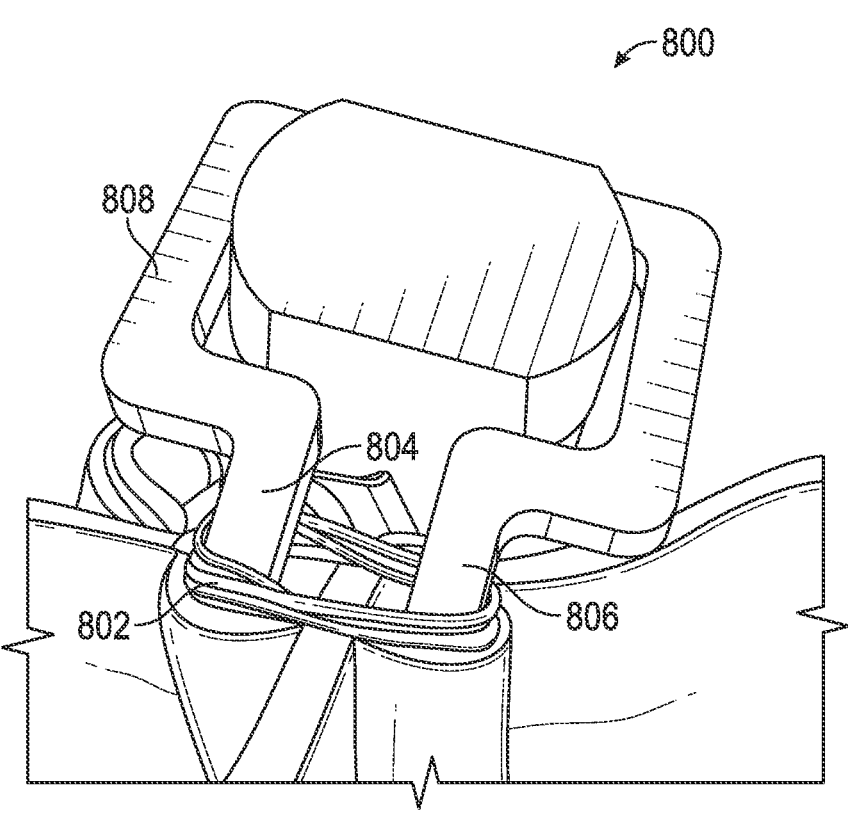
FIG. 46 is a perspective view of a commissure illustrating the first and second members of a commissure support element tied together with sutures, according to another embodiment.

FIG. 46 illustrates a commissure support element 800 configured similarly to the support element 400 comprising sutures 802 wrapped around members 804 and 806 coupling the collar portion 808 to the axial members.

Figure 48:
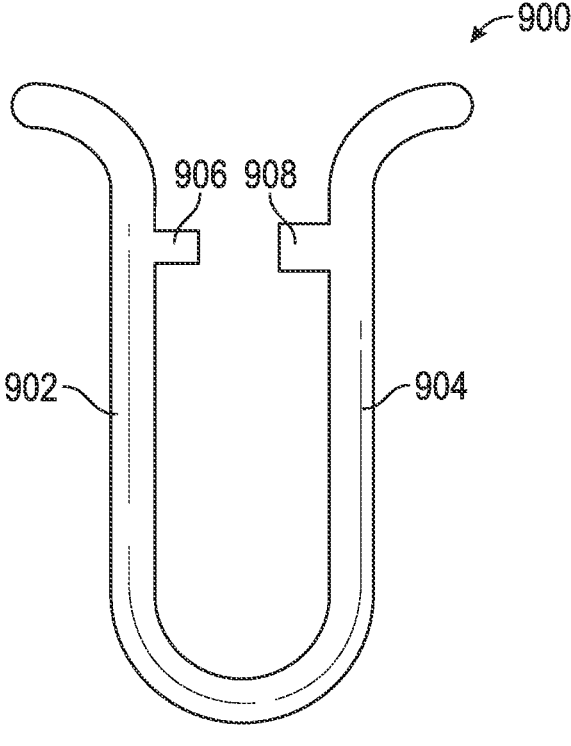
FIG. 48 is a front elevation view of a commissure support element in which the first and second members include opposing projections, according to another embodiment.

FIG. 48 illustrates another embodiment of a commissure support element 900 configured similarly to the support element 700, wherein the first and second axial members 902 and 904 comprise opposing protrusions 906 and 908 that can contact each other to limit the degree to which the axial members may deflect toward one another (e.g., when suture is tied around them as in FIG. 45).

FIG. 49 illustrates another embodiment of a commissure support member 1000 configured similarly to the support element 700, and in which the first and second axial members 1002, 1004 comprise complementary clasp members 1006 and 1008. When engaged, the clasp members 1006 and 1008 can prevent the axial members 1002 and 1004 from moving apart. The length of the clasp members 1006 and 1008 can determine the spacing of the axial members 1002 and 1004, and the pressure applied to leaflets received between them.

FIG. 50A illustrates another embodiment of a commissure support element 1100 configured similarly to the support element 700, wherein the first and second axial members 1102 and 1104 comprise flexible tab portions 1106 and 1108 extending along at least a portion of the length of the axial members, and extending inwardly toward each other across the leaflet-receiving window 1110. The tab portions 1106 and 1108 can comprise a flexible material, and can be sized such that when leaflets are inserted between the axial members, the tab portions rotate or flex radially inwardly (or radially outwardly) to resiliently engage the leaflets. FIG. 50B is a schematic cross-sectional view of the first and second axial members 1102 and 1104 showing the flexible tab portions 1106 and 1108 in their neutral, undeflected position, and in their rotated or deflected position 1106' and 1108'. In certain embodiments, the flexible tab portions 1106 and 1108 can rotate about their central axes. In certain embodiments, the flexible tab portions 1106 and 1108 can be integrally formed with the first and second axial members 1102 and 1104, or separately formed and attached to the axial members, depending upon the particular characteristics desired.

Figure 51:
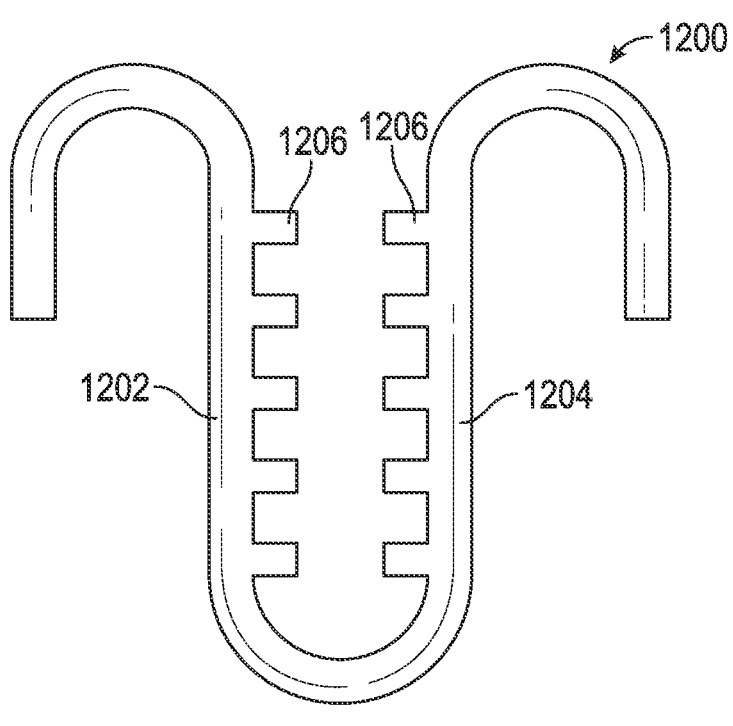
FIG. 51 is a front elevation view of a commissure support element in which the first and second members include a plurality of opposed projections, according to one embodiment.

FIG. 51 illustrates another embodiment of a commissure support element 1200 configured similarly to the support element 700, wherein the first and second axial members 1202 and 1204 comprise a plurality of projections, protrusions, notches, teeth, serrations, or tabs 1206 on the inner aspect of the members and arranged in an opposing manner. The projections 1206 can be configured to frictionally engage leaflets inserted between the axial members.

Figure 52:
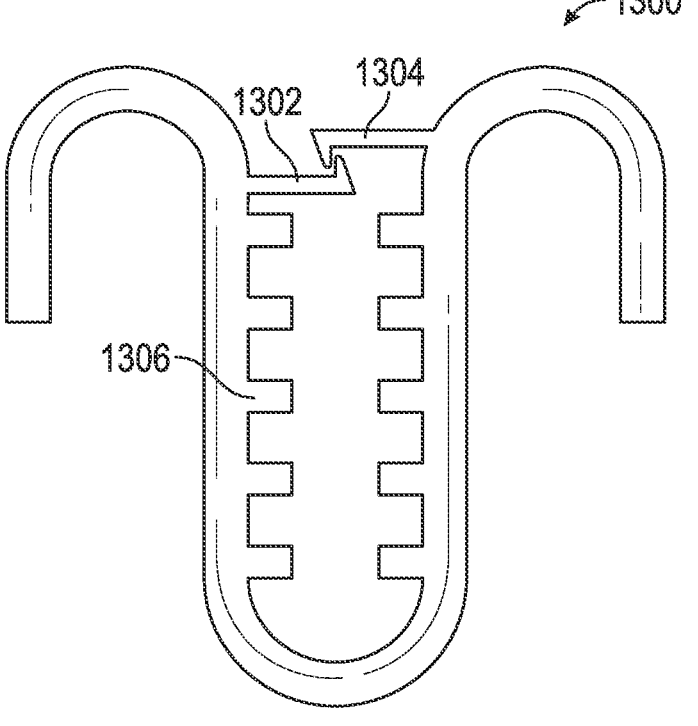
FIG. 52 is a front elevation view of a commissure support element in which the first and second members include opposed projections and clasps.
Figure 53:
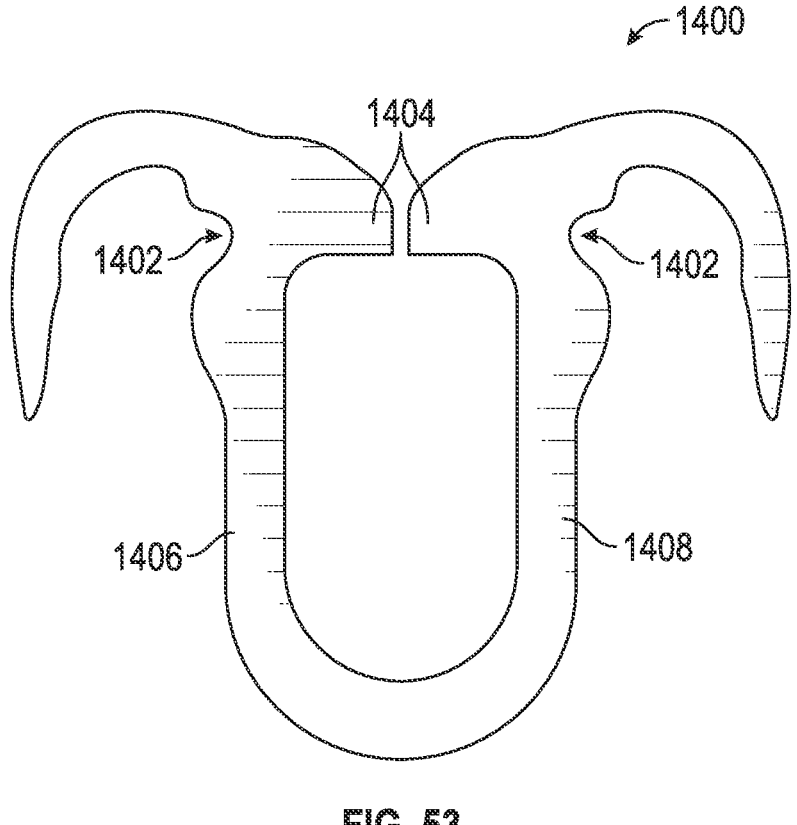
FIG. 53 is a front elevation view of a commissure support element in which the first and second members include notches and opposed projections, according to another embodiment.

The features described above may be combined in any of various combinations. In one non-limiting example, FIG. 52 illustrates an embodiment of a commissure support element 1300 comprising clasp elements 1302 and 1304 similar to the clasps 1006 and 1008 of FIG. 49 in combination with projections 1306 similar to the projections 1206 of FIG. 51. FIG. 53 illustrates another embodiment in which the commissure support element 1400 comprises suture retaining notches 1402 for retaining sutures and protrusions 1404 configured to maintain a minimum spacing between the axial members 1406 and 1408. Any combination of any number of the features described herein is contemplated by this disclosure.

As noted above, any of the commissure support elements disclosed herein can be formed by bending a piece of wire (e.g., a straight piece of wire) into the specified shape and securing the free ends of the wire together, such as by welding. The commissure support elements can also be formed using other techniques including, for example, molding (e.g., injection molding), machining (e.g., laser cutting), and/or 3D printing, and bending or folding the elements into the specified shape as needed.

Although the commissure support elements disclosed herein have been described as being mounted on an actuator component of a prosthetic valve, any of the commissure support elements disclosed herein can be mounted on other portions of a prosthetic valve. For example, a frame of a prosthetic valve can have axially extending posts that are separate from the actuator components for mounting the commissure support elements. In one specific embodiment, a frame can have a plurality of posts corresponding to the number of commissures (e.g., three posts for three commissures), with each post being mounted to the inner surface of the frame (e.g., to selected struts 26 of the frame) between two adjacent actuator components 32.

Further, the commissure support elements described herein may also be used with prosthetic heart valves that do not have actuators, such as self-expandable prosthetic heart valves or plastically-expandable prosthetic heart valves (e.g., such as those that are expanded to their functional size by inflating a balloon). Examples of self-expandable prosthetic heart valves can be found in U.S. Pat. Nos. 8,652,202, 9,155,619, and U.S. Publication No. 2014/0343670, which are incorporated herein by reference. Examples of plastically-expandable prosthetic heart valves can be found in U.S. Pat. No. 9,393,110, and U.S. Publication No. 2018/0028310, which are incorporated herein by reference.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of a prosthetic valve is its inflow end and the upper end of the prosthetic valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

Unless otherwise indicated, all numbers expressing quantities of components, molecular weights, percentages, temperatures, forces, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A prosthetic heart valve, comprising:

an annular frame comprising a plurality of angled strut members, the frame being radially collapsible to a collapsed configuration and radially expandable to an expanded configuration, the frame having an inflow end and an outflow end;

a leaflet structure positioned at least partially within the frame, the leaflet structure comprising a plurality of leaflets arranged to form a plurality of commissures;

a plurality of axially extending posts coupled to an inner surface of the frame; and a plurality of commissure support elements, each commissure support element comprising a unitary wire member, each commissure support element being positioned at one of the commissures, each of the commissure support elements comprising a coupling portion coupled to the frame and first and second members coupled to the coupling portion and extending in a direction toward the inflow end of the frame or toward the outflow end of the frame, the leaflets of each commissure being received between the first and second members of the respective commissure support element;

wherein the first and second members are joined together distally of the coupling portion and define a leaflet-receiving space through which leaflets are received.

2. The prosthetic heart valve of claim 1, wherein the coupling portion comprises an annular collar portion.

3. The prosthetic heart valve of claim 2, wherein the collar portion of the commissure support element at each commissure is disposed around the post at the commissure.

4. The prosthetic heart valve of claim 2, wherein the first and second members are coupled together radially inwardly of the post.

5. The prosthetic heart valve of claim 4, wherein:

the first and second members are spaced radially inwardly from the post; and leaflets of the commissures are sutured to the first and second members of the respective commissure support elements in a space between the post and the first and second members.

6. The prosthetic heart valve of claim 5, wherein the first and second members are coupled to the collar portion by curved members that curve in a direction of the outflow end of the frame.

7. The prosthetic heart valve of claim 6, wherein the collar portion comprises at least one protrusion configured to engage a corresponding recess in the post.

8. The prosthetic heart valve of claim 7, wherein each of the first and second members comprise at least one opening.

9. The prosthetic heart valve of claim 8, wherein the posts comprise recesses configured to receive the collar portions of the commissure support elements.

10. The prosthetic heart valve of claim 9, wherein the coupling portion is rectangular.

11. The prosthetic heart valve of claim 8, wherein:

the collar portion is a first collar portion; and the first and second members are joined together radially outwardly of the post to form a second collar portion longitudinally spaced apart from the first collar portion.

12. The prosthetic heart valve of claim 11, wherein the first and second members of each commissure support element are clamping members rotatable away from the post to receive a leaflet.

13. The prosthetic heart valve of claim 12, wherein the posts comprise grooves configured to receive the first and second collar portions of the commissure support elements.

14. The prosthetic heart valve of claim 13, wherein the first and second collar portions are angled toward each other.

15. The prosthetic heart valve of claim 14, wherein each leaflet is folded to form a cuff that is circumferentially offset from the respective clamping member that clamps the leaflet against the frame.

16. The prosthetic heart valve of claim 15, wherein the cuff of each leaflet is configured to contact the frame to prevent rotation of the leaflet about the respective clamping member by which it is clamped against the frame during operation of the prosthetic heart valve.

17. The prosthetic heart valve of claim 16, wherein the cuffs comprise folded edges oriented radially inward toward a center of the prosthetic heart valve.

18. The prosthetic heart valve of claim 17, wherein the first and second collar portions of the commissure support element have a shape that conforms to a shape of the posts.

19. The prosthetic heart valve of claim 1, wherein the coupling portion comprises a first coupling member and a second coupling member configured to engage the frame.

20. The prosthetic heart valve of claim 19, wherein the first coupling member and the second coupling member are received in the post at the commissure.

21. The prosthetic heart valve of claim 20, wherein the post defines channels configured to receive the first coupling member and the second coupling member.

22. The prosthetic heart valve of claim 21, wherein the first and second members extend in a direction toward the outflow end of the frame.

23. The prosthetic heart valve of claim 22, wherein the first and second coupling members comprise projections configured to engage the post.

24. The prosthetic heart valve of claim 23, wherein the first member comprises a clasp configured to engage a clasp of the second member.

25. The prosthetic heart valve of claim 24, further comprising suture extending between the first and second members to clamp the leaflets between the first and second members.

26. The prosthetic heart valve of claim 22, wherein the first and second members of the commissure support elements each comprise flexible tab portions resiliently engaging the leaflets at each respective commissure.

27. The prosthetic heart valve of claim 22, wherein the first and second members of the commissure support elements comprise projections that engage the leaflets of the respective commissure.

28. The prosthetic heart valve of claim 3, wherein:

the frame is a mechanically expandable frame and the posts comprise components of actuators configured to radially expand and collapse the frame; and the collar portion of the commissure support element at each commissure is disposed around the actuator component at the commissure.

* * * * *